US010426147B2

(12) United States Patent
Koukidou et al.

(10) Patent No.: US 10,426,147 B2
(45) Date of Patent: Oct. 1, 2019

(54) INSECT MUSCLE ACTIN PROMOTER

(71) Applicant: Oxitec Limited, Abingdon, Oxfordshire (GB)

(72) Inventors: Martha Koukidou, Abingdon (GB); Sarah Scaife, Abingdon (GB); Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 81 days.

(21) Appl. No.: 15/632,213

(22) Filed: Jun. 23, 2017

(65) Prior Publication Data

US 2017/0360015 A1 Dec. 21, 2017

Related U.S. Application Data

(63) Continuation of application No. 14/773,252, filed as application No. PCT/EP2014/054290 on Mar. 5, 2014, now abandoned.

(30) Foreign Application Priority Data

Mar. 5, 2013 (GB) .................................. 1303932.6

(51) Int. Cl.
A01K 67/033 (2006.01)
C07K 14/435 (2006.01)
C12N 15/85 (2006.01)

(52) U.S. Cl.
CPC .... *A01K 67/0339* (2013.01); *C07K 14/43577* (2013.01); *C07K 14/43586* (2013.01); *C12N 15/8509* (2013.01); *A01K 2217/05* (2013.01); *A01K 2227/706* (2013.01); *A01K 2267/0393* (2013.01); *C12N 2800/105* (2013.01); *C12N 2830/008* (2013.01)

(58) Field of Classification Search
CPC ................................................ A01K 67/0339
See application file for complete search history.

(56) References Cited

U.S. PATENT DOCUMENTS

| | | |
|---|---|---|
| 5,254,801 A | 10/1993 | Dotson et al. |
| 5,278,057 A | 1/1994 | Jorgensen |
| 5,670,353 A | 9/1997 | Ahlquist et al. |
| 5,674,747 A | 10/1997 | Hammock et al. |
| 5,773,697 A | 6/1998 | Tomes et al. |
| 5,851,796 A | 12/1998 | Schatz |
| 5,977,441 A | 11/1999 | Oliver et al. |
| 6,200,800 B1 | 3/2001 | Choulika et al. |
| 6,235,278 B1 | 5/2001 | Miller et al. |
| 6,338,040 B1 | 1/2002 | Buman et al. |
| 6,962,810 B2 | 11/2005 | Fraser et al. |
| 7,998,475 B2 | 8/2011 | Alphey |
| 8,124,404 B2 | 2/2012 | Alphey |
| 9,121,036 B2 | 9/2015 | Alphey |
| 9,125,388 B2 | 9/2015 | Alphey |
| 9,133,477 B2 | 9/2015 | Alphey |
| 9,487,801 B2 | 11/2016 | Alphey et al. |
| 2003/0150007 A1 | 8/2003 | Savakis et al. |
| 2003/0213005 A1 | 11/2003 | Alphey et al. |
| 2004/0082032 A1 | 4/2004 | Bovi et al. |
| 2005/0221430 A1 | 10/2005 | Prentice |
| 2006/0212949 A1 | 9/2006 | Alphey |
| 2006/0242717 A1 | 10/2006 | Alphey |
| 2006/0275276 A1 | 12/2006 | Alphey |
| 2007/0056051 A1 | 3/2007 | Alphey |
| 2008/0115233 A1 | 5/2008 | Alphey et al. |
| 2009/0170793 A1 | 7/2009 | Gaur |
| 2009/0183269 A1 | 7/2009 | Alphey |
| 2013/0298266 A1 | 11/2013 | Alphey et al. |

FOREIGN PATENT DOCUMENTS

| | | |
|---|---|---|
| EP | 0 636 310 | 2/1995 |
| EP | 0 955 364 | 11/1999 |
| GB | 2 355 459 | 4/2001 |
| GB | 2 404 382 | 2/2005 |
| GB | 2 443 186 | 4/2008 |
| GB | 2 500 113 | 9/2013 |
| JP | 2008-067678 | 3/2008 |
| WO | WO-1990/008830 | 8/1990 |
| WO | WO-1994/003619 | 2/1994 |
| WO | WO-1996/004393 | 2/1996 |
| WO | WO-1996/024605 | 8/1996 |
| WO | WO-1997/030162 | 8/1997 |
| WO | WO-1998/008960 | 3/1998 |
| WO | WO-1999/010488 | 3/1999 |
| WO | WO-2000/073510 | 12/2000 |
| WO | WO-2001/039599 | 6/2001 |

(Continued)

OTHER PUBLICATIONS

"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Adelman et al., "Formation and loss of large, unstable tandem arrays of the piggyBac transposable element in the yellow fever mosquito, *Aedes aegypti*," Transgenic Res (2004) 13(5):411-425.
Alignment of SEQ ID No. 22 of D1 (WO 2005/012534) with tTAV, Jul. 4, 2014.
Allen et al., "Flight muscle-specific expression of act88F: GFP in transgenic Culex quinquefasciatus Say (Diptera: Culicidae)," Parasitology Int (2004) 53(4):307-314.
Allen et al., "PiggyBac transformation of the New World screwworm, *Cochliomyia hominivorax*, produces multiple distinct mutant strains," Med. Vet. Entomol (2004) 18:1-9.

(Continued)

*Primary Examiner* — Thaian N Ton
*Assistant Examiner* — David A. Montanari
(74) *Attorney, Agent, or Firm* — Patrick J. Farley; Intrexon Corporation

(57) ABSTRACT

Provided is a gene expression system, suitable for expression in an insect, comprising an insect muscle actin promoter operably linked to a marker gene, which overcomes or ameliorates one or more of: cost of rearing; amount of handling; errors in identification due to human error or loss of marker by the insect; and health concerns related to the effects of marker powders on workers in mass rearing facilities.

19 Claims, 7 Drawing Sheets

Specification includes a Sequence Listing.

(56) References Cited

FOREIGN PATENT DOCUMENTS

| WO | WO-2001/059088 | 8/2001 |
|----|----------------|--------|
| WO | WO-2001/091802 | 12/2001 |
| WO | WO-2002/046444 | 6/2002 |
| WO | WO-2002/101061 | 12/2002 |
| WO | WO-2004/044150 | 5/2004 |
| WO | WO-2004/098278 | 11/2004 |
| WO | WO-2004/108933 | 12/2004 |
| WO | WO-2005/003364 | 1/2005 |
| WO | WO-2005/012534 | 2/2005 |
| WO | WO-2007/091099 | 8/2007 |
| WO | WO-2008/134068 | 11/2008 |
| WO | WO-2009/016627 | 2/2009 |
| WO | WO-2009/115569 | 9/2009 |
| WO | WO-2009/157771 | 12/2009 |
| WO | WO-2013/131920 | 9/2013 |

OTHER PUBLICATIONS

Allen et al., "Stable, germ-line transformation of Culex quinquefasciatus (Diptera: Culicidae)," J Med Entomol (2001) 38(5):701-710.
Alphey et al. (May 2002) "Dominant Lethality and Insect Population Control," Mol. Biochem. Parasitol. 121(2):173-178.
Alphey et al., "Malaria control with genetically manipulated insect vectors," Science (2002) 298:119-21.
Alphey et al., "Modeling resistance to genetic control of insects," Journal of Theoretical Biology (2011) 270:42-55.
Alphey et al., "Managing Insecticide Resistance by Mass Release of Engineered Insects," J. Econ. Entomol. (2007) 100(5):1642-1649.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique," BMC Biology (2012) 10:51, 8 pages.
Arama et al., "Caspase activity and a specific cytochrome C are required for sperm differentiation in Drosophila," Dev Cell (2003) 4(5):687-97.
Arribas et al., "The ubiquitin genes in D. melanogaster: transcription and polymorphism," Biochimica et Biophysica Acta (1986) 868:119-127.
Atkinson et al., "Genetic transformation systems in insects," Annu Rev Entomol (2001) 46:317-346.
Atkinson et al., "Hermes and Other hAT Elements as Gene Vectors in Insects," in: Insect Transgenesis: Methods and Applications, Hadler et al. (eds.), Boca Raton CRC Press (2000) pp. 219-235.
Barreau et al., "Post-meiotic transcription in Drosophila testes," Development (2008) 135(11):1897-1902.
Bauer Dumont et al., "Recurrent positive selection at bgcn, a key determinant of germ line differentiation, does not appear to be driven by simple coevolution with its partner protein bam," Mol Biol Evol (2007) 24(1):182-191.
Beall et al., "Discovery of tMAC: a Drosophila testis-specific meiotic arrest complex paralogous to Myb-Muv B," Genes Dev (2007) 21(8):904-919.
Bello et al., "Spatial and temporal targeting of gene expression in Drosophila by means of a tetracycline-dependent transactivator system," Development (1998) 125(12):2193-2202.
Berghammer et al., "A universal marker for transgenic insects," Nature (1999) 402(6760):370-371.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Beullens et al., "The isolation of novel inhibitory polypeptides of protein phosphatase 1 from bovine thymus nuclei," J Biol Chem (1992) 267(23):16538-16544.
Beumer et al., "Efficient gene targeting in Drosophila with zinc-finger nucleases," Genetics (2006)172(4):2391-2403.
Bibikova et al., "Targeted chromosomal cleavage and mutagenesis in Drosophila using zinc-finger nucleases," Genetics (2002)161(3):1169-1175.
Bieschke et al. (Jun. 1998) "Doxycycline-Induced Transgene Expression During Drosophila Development and Aging," Mol. Gen Genet. 258(6):571-579.
Black et al., "Why RIDL is not SIT," Trends Parasitol (2011) 27(8):362-370.
Blitvich et al., "Developmental- and tissue-specific expression of an inhibitor of apoptosis protein 1 homologue from Aedes triseriatus mosquitos," Insect Molecular Biology (2002) 11(5):431-442.
Boudrez et al., "Identification of MYPT1 and NIPP1 as subunits of protein phosphatase 1 in rat liver cytosol," FEBS Letters 455 (1999) 175-178.
Brand et al., "Ectopic expression in Drosophila," Methods Cell Biol (1994)44:635-654.
Brand et al., "Targeted gene expression as a means of altering cell fates and generating dominant phenotypes," Development (1993) 118(2):401-415.
Burcin et al., "A regulatory system for target gene expression," Frontiers in Biosc. (1998) 3:c1-7.
Burn et al., "Alternative 5C actin transcripts are localized in different patterns during Drosophila embryogenesis," Dev Biol (1989) 131(2):345-355.
Burt et al., "Site-specific selfish genes as tools for the control and genetic engineering of natural populations," Proc Biol Sci (2003) 270:921-928.
Cabrera et al., "Expression Pattern of Gal4 Enhancer Trap Insertions into the bric a brac Locus Generated by P Element Replacement," Genesis (2002) 34:62-65.
Caceres et al., "Mass rearing of temperature sensitive genetic sexing strains in the Mediterranean fruit fly (Ceratitis capitata)," Genetica (2002) 115(1):107-116.
Cagan et al., "Spermatogenesis: Borrowing the Apoptotic Machinery," Curr Biol (2003)13:R600-R602.
Carriere and Tabashnik, "Reversing Insect Adaptation to Transgenic Insecticidal Plants," Proc. R. Soc. Lond. B. (2001) 268:1475-1480.
Catteruccia et al., "An Anopheles transgenic sexing strain for vector control," Nat Biotechnol, (2005) 23(11):1414-1417.
Catteruccia et al., "Impact of genetic manipulation on the fitness of Anopheles stephensi mosquitoes," Science (2003) 299(5610):1225-1227.
Catteruccia et al., "Stable germline transformation of the malaria mosquito Anopheles stephensi," Nature (2000) 405(6789):959-962.
Catteruccia et al., "Transgenic technologies to induce sterility," Malaria Journal (2009)8 (Supp2)S7.
Cenik et al., "Genome analysis reveals interplay between 5'UTR introns and nuclear mRNA export for secretory and mitochondrial genes," PLoS Genet (2011) 794:e1001366.
Cha et al., "Expression of green fluorescent protein in insect larvae and its application for heterologous protein production," Biotechnol Bioeng (1997) 56(3):239-247.
Chalfie et al., "Green fluorescent protein as a marker for gene expression," Science (1994) 263(5148):802-805.
Chen et al. (Oct. 2000) "The Use of Modified Tetracycline Regulatory Expression System with Reduced Basal Level to Develop and In Vivo Biopesticide Expression System," Food Sci Agricult. Chem. 2(4):220-225.
Chen et al., "Apoptotic Activity of REAPER is Distinct from Signaling by the Tumor Necrosis Factor Receptor 1 Death Domain," The Journal of Biological Chemistry (1996) 271(42):25735-25737.
Cheng et al., "Cellular transformation by Simian Virus 40 and Murine Polyoma Virus T antigens," Semin Cancer Biol (2009) 19(4):218-228.
Chintapalli et al., "Using FlyAtlas to identify better Drosophila melanogaster models of human disease," Nature Genetics (2007) 39(6)715-720.
Cho, "Enhancers," WIREs Dev Biol (2012) 1:469-478.
Curtis et al., "Assessment of the impact of potential tetracycline exposure on the phenotype of Aedes aegypti 0X513A: Implications for field use," PLOS Negelcted Tropical Diseases (2015) 9(8):e0003999.

(56) References Cited

OTHER PUBLICATIONS

Davis et al., "Engineered Underdominance Allows Efficient and Economical Introgression of Traits into Pest Populations," J. Theor. Biol. (2001) 212(1):83-98.
Definition of "pest" from the Concise Oxford American Dictionary (2006) p. 661.
Deng et al., "A targeted gene silencing technique shows that *Drosophila* myosin VI is required for egg chamber and imaginal disc morphogenesis," J Cell Science (1999) 112:3677-3690.
Deredec et al., "The population genetics of using homing endonuclease genes in vector and pest management," Genetics (2008) 179(4):2013-2026.
Devault et al., "Biotechnology and new integrated pest management approaches," Nature Biotechnology (1996) 14:46-49.
Dhillon et al., "The melon fruit fly, *Bactrocera cucurbitae*: A review of its biology and management," J Insect Sci (2005) 5:40.
Egloff et al., "Structural basis for the recognition of regulatory subunits by the catalytic subunit of protein phosphatase 1," EMBO J (1997) 16(8):1876-1887.
Elick et al., "Analysis of the Cis-Acting DNA Elements Required for piggyback Transposable Element Excision," Mol. Gen. Genet. (1997) 255:605-610.
Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt I Main, BRD.
Flaminia et al., "Transgenic technologies to induce sterility," Malar J. (2009) 8 Suppl 2:S7.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Franz, "Recombination between homologous autosomes in medfly (*Ceratitis capitata*) males: type-1 recombination and the implications for the stability of genetic sexing strains," Genetica (2002) 116(1):73-84.
Fraser,"Insect transgenesis: current applications and future prospects," Annu Rev Entomol (2012) 57:267-289.
Fryxell et al., "Autocidal biological control: a general strategy for insect control based on genetic transformation with a highly conserved gene," J Econ Entomol (1995) 88(5):1221-1232.
Fu et al., "Female-specific flightless phenotype for mosquito control," Proc Natl Acad Sci USA (2010) 107(10):4550-4554.
Fu et al., "Female-specific insect lethality engineered using alternative splicing," Nature Biotechnology (2007) 25(3):353-357.
Fuller, "Spermatogenesis," in: The Development of *Drosophila melanogaster*, Bate et al., Cold Spring Harbor Laboratory Press (1993) pp. 71-147.
Funaguma et al., "The Bmdsx transgene including trimmed introns is sex-specifically spliced in tissues of the silkworm, *Bombyx mori*," Journal of Insect Science (online) (2005) 5(17):1-6.
Fussenegger et al. (1998) "Regulated Multicistronic Expression Technology for Mammalian Metabolic Engineering," Cytotechnology 28:111-126.
Fussenegger et al., "Streptogramin-based gene regulation systems for mammalian cells," Nat Biotechnol (2000) 18(11):1203-1208.
Fussenegger et al., "The impact of mammalian gene regulation concepts on functional genomic research, metabolic engineering, and advanced gene therapies," Biotechnol Prog (2001) 17(1):1-51.
Fussenegger et al., "Autoregulated multicistronic expression vectors provide one-step cloning of regulated product gene expression in mammalian cells," Biotechnol. Prog. (1997) 13:733-740.
Fux et al. (2003) "Novel Macrolide-Adjustable Bidirectional Expression Modules for Coordinated Expression of Two Different Transgenes in Mice," J Gene Medicine 5:1067-1079.
Ghosh et al., "Transcription factor binding and induced transcription alter chromosomal c-myc replicator activity," Mol Cell Biol (2004) 24(23):10193-10207.

Gloor et al., "Targeted Gene Replacement in *Drosophila* Via P Element-Induced Gap Repair," Science (1991) 253:1110-1117.
Golovnin et al., "The su(Hw) insulator can disrupt enhancer-promoter interactions when located more than 20 kilobases away from the *Drosophila* achaete-scute complex," Mol Cell Biol (1999) 19(5):3443-3456.
Gonczy et al., "Bag-of-marbles and benign gonial cell neoplasm act in the germline to restrict proliferation during *Drosophila* spermatogenesis," Development (1997) 124(21):4361-4371.
Gong et al., "A dominant lethal genetic system for autocidal control of the Mediterranean fruit fly," Nat Biotechnol (2005) 23(4):453-456.
Gong et al., "Ends-out, or replacement, gene targeting in *Drosophila*," Proc Natl Acad Sci (USA) (2003) 100(5):2556-2561.
Gonzy-Treboul et al., "Enhancer-Trap Targeting at the Broad-Complex Locus of *Drosophila melanogaster*," Genes Dev. (1995) 9:1137-1148.
Gossen et al., "Studying gene function in eukaryotes by conditional gene inactivation," Annu Rev Genet (2002) 36:153-173.
Gossen et al., "Tight control of gene expression in mammalian cells by tetracycline-responsive promoters," Proc Natl Acad Sci (USA) (1992) 89(12):5547-5551.
Gossen et al., Tetracycline in Biology, Chemistry and Medicine (2001) pp. 139-157.
Graham et al., "Larval diets containing dyes for tagging pink bollworm moth internally," J Econ Entomol (1971) 64:376-379.
Great Britain Application No. 1303932.6, filed Mar. 5, 2013, 42 pages.
"GSN: AAD40186" Oct. 22, 2002 [Retrieved from the internet: http://ibis.internal.epo.org/exam/dbfetch.jsp?id=GSN:AAD40186] retrieved on Nov. 28, 2017.
"GSN: BB010346" Nov. 6, 2014 [Retrieved from the internet: http://ibis.internal.epo.org/exam/dbfetch.jsp?id=GSN:BB010346] retrieved on Nov. 28, 2017.
Guo et al., "Species-specific signals for the splicing of a short *Drosophila* intron in vitro," Mol Cell Biol (1993) 13(2):1104-1118.
Hagler et al., "Methods for marking insects: current techniques and future prospects," Annu. Rev. Entomol. (2001) 46:511-543.
Hagler et al., "An Alternative to conventional insect marking procedures; detection of a protein mark on pink bollworm by ELISA," Entomol Exp Appl (2002) 103(1):1-9.
Han et al., PNAS (2011) 108:9673-9678.
Handler et al., "Germline transformation of *Drosophila melanogaster* with the piggyBac transposon vector," Insect Mol Biol (1999) 8(4):449-457.
Handler et al., "Polyubiquitin-regulated DsRed marker for transgenic insects," BioTechniques (2001) 31:820-828.
Handler et al., "Prospects for using genetic transformation for improved SIT and new biocontrol methods," Genetics (2002) 116:137-149.
Handler et al., "A Current Prospective on Insect Gene Transformation," Insect Biochem. Mol. Biol. (2001) 31(2):111-128.
Handler et al., "Use of piggyback Transposon for Germ-Line Transformation of Insects," Insect Biochem. Mol. Biol. (2002) 32:1211-1220.
Handler et al., "The lepidopteran transposon vector, piggyBac, mediates germ-line transformation in the Mediterranean fruit fly," PNAS (1998) 95:7520-7525.
Harris et al., "Field performance of engineered male mosquitoes," Nature Biotechnology (2011) 29(11):1034-1039.
He et al., "The actin gene family in the oriental fruit fly *Bactrocera dorsalis*. Muscle specific actins," Insect Biochem Mol Biol (1994) 24(9):891-906.
Heinrich et al. (Jul. 18, 2000) "A Repressible Female-Specific Lethal Genetic System for Making Transgenic Insect Strains Suitable for a Sterile-Release Program," Proc. Nat. Acad. Sci. USA 97:8229-8232.
Heslip et al., "Targeted Transposition at the vestigial Locus of *Drosophila melanogaster*," Genetics (1994) 138:1127-1135.
Hiller et al., "Testis-specific TAF homologs collaborate to control a tissue-specific transcription program," Development (2004) 131:5297-5308.

(56) References Cited

OTHER PUBLICATIONS

Hockemeyer et al., "Genetic engineering of human pluripotent cells using TALE nucleases," Nat Biotechnol (2011) 29(8):731-734.
Hofmann et al. (1996) "Rapid Retroviral Delivery of Tetracycline-Inducible Genes in a Single Autoregulatory Cassette," Proc. Nat. Acad. Sci. USA 93:5185-5190.
Hondred et al., "Use of Ubiquitin Fusions to Augment Protein Expression in Transgenic Plants," Plant Physiology (1999) 119:713-723.
Horn et al., "A transgene-based, embryo-specific lethality system for insect pest management," Nat Biotechnol (2003) 1:64-70.
Horn et al., "Fluorescent transformation markers for insect transgenesis," Insect Biochemistry and Molecular Biology (2002) 32:1221-1235.
Horn et al., "Highly sensitive, fluorescent transformation marker for *Drosophila* transgenesis," Dev. Genes Evol. (2000) 210:623-629.
Horn et al., "piggyBac-Based Insertional Mutagenesis and Enhancer Detection as a Tool for Functional Insect Genomics," Genetics (2003) 163:647-661.
Imai, "Control of insecticide resistance in a filed population of houseflies, *Musca domestica*, by releasing susceptible flies," Res. Popul. Ecol. (1987) 29:129-146.
Inoue et al., "Binding of the *Drosophila* Sex-lethal gene product to the alternative splice site of transformer primary transcript," Nature (1990) 344:461-463.
International Preliminary Report on Patentability for PCT/EP2014/054290, dated Sep. 8, 2015, 7 pages.
International Preliminary Report on Patentability for PCT/GB2007/000488, dated May 5, 2008, 11 pages.
International Preliminary Examination Report for PCT/GB00/04541, dated Apr. 4, 2002, 2 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2004/003263, dated Jan. 30, 2006, 6 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion for PCT/GB2015/051633, dated Oct. 8, 2015, 11 pages.
International Search Report for PCT/GB2000/04541, dated Nov. 19, 2001.
International Search Report for PCT/GB2004/003263, dated Nov. 5, 2004, 3 pages.
International Search Report for PCT/GB2007/000488, dated Jun. 6, 2007, 3 pages.
International Search Report for PCT/GB2004/002869, dated Jan. 11, 2005, 5 pages.
International Search Report for PCT/GB2004/002021, dated Oct. 6, 2004, 3 pages.
Irvin et al., "Assessing fitness costs for transgenic Aedes aegypti expressing the GFP marker and transposase genes," Proc Natl Acad Sci U.S.A. (2004) 101(3):891-896.
Jagiello et al., "NIPP-1, a nuclear inhibitory subunit of protein phosphatase-1, has RNA-binding properties," J Biol Chem (1997) 272(35):22067-22071.
Jattani et al., "Deficiency screen identifies a novel role for beta 2 tubulin in salivary gland and myoblast migration in the *Drosophila* embryo," Dev Dyn (2009) 238(4):853-863.
Jiang et al., "Tombola, a tesmin/TSO1-family protein, regulates transcriptional activation in the *Drosophila* male germline and physically interacts with always early," Development (2007) 134(8):1549-1559.
Jiang et al., "Transcriptional activation in *Drosophila* spermatogenesis involves the mutually dependent function of aly and a novel meiotic arrest gene cookie monster," Development (2003) 130(3):563-573.
Jin et al., "Engineered female-specific lethality for control of pest lepidoptera," ACS Synthetic Biology, ACS (2013) 1(3):160-66.
Jin et al., "Mapping of the RNA-binding and endoribonuclease domains of NIPP1, a nuclear targeting subunit of protein phosphatase 1," Biochem J (1999) 342:13-19.
Johnson-Schlitz et al., "P-element-induced interallelic gene conversion of insertions and deletions in *Drosophila melanogaster*," Molecular and Cellular Biology (1993) 13(11):7006-7018.
Kawase et al., "Gbb/Bmp signaling is essential for maintaining germline stem cells and for repressing bam transcription in the *Drosophila* testis," Development (2004) 131(6):1365-1375.
Kelly et al., "*Drosophila* MEF2 is a direct regulator of Actin57B transcription in cardiac, skeletal, and visceral muscle lineages," Mech Dev (2002) 110(1-2):39-50.
Kim et al., "Hybrid restriction enzymes: zinc finger fusions to Fok I cleavage domain," Proc Natl Acad Sci (USA) (1996) 93:1156-1160.
Klassen, "History of the Sterile Insect Technique," in: Sterile Insect Technique, Principles and Practice in Area-Wide Integrated Pest Management, Curits et al., (eds) The Netherlands, Springer (2005) pp. 3-36.
Knipling et al., "Possibilities of Insect Control or Eradication Through the Use of Sexually Sterile Males," J Econ Entomol (1955) 48:459-462.
Koukidou et al., "Germ line transformation of the olive fly *Bactrocera oleae* using a versatile transgenesis marker," Insect Mol Biol (2006) 15(1):95-103.
Krafsur, "Bionomics of the face fly, *Musca autumnalis*," Annu Rev Entomol (1997) 42:503-523 (Abstract).
Lankenau et al., "Comparison of Targeted-Gene Replacement Frequencies in *Drosophila melanogaster* at the forked and white Loci," Molecular and Cellular Biology (1996) 16(7):3535-44.
Loew et al., "Improved tet-responsive promoters with minimized background expression," BMC Biotechnology (2010) 10:81.
Louis et al. (Nov. 2003) "A Theoretical Model for the Regulation of Sex-Lethal, a Gene That Controls Sex Determination and Dosage Compensation in *Drosophila melanogaster*," Genetics 165:1355-1384.
Loukeris et al., "Gene transfer into the medfly, *Ceratitis capitata*, with a *Drosophila hydei* transposable element," Science (1999) 270(5244):2002-2005.
Loukeris et al., "Introduction of the transposable element Minos into the germ line of *Drosophila melanogaster*," PNAS (1995) 92:9485-9489.
Lycett et al., "Conditional expression in the malaria mosquito *Anopheles stephensi* with Tet-On and Tet-Off systems," Genetics (2004) 167(4):1781-1790.
Mahfouz et al., "De novo-engineered transcription activator-like effector (TALE) hybrid nuclease with novel DNA binding specificity creates double-strand breaks," Proc Natl Acad Sci (USA) (2011) 101(6):2623-2628.
Malacrida et al., "A transgenic sperm marking system in the medfly, as a tool for pest control strategies and sperm use analysis," Entomological Research (2007) 37:A56.
Marrelli et al., "Mosquito transgenesis: what is the fitness cost?" Trends Parasitol (2006) 22(5):197-202.
Mattox et al., "Alternative splicing of the sex determination gene transformer-2 is sex-specific in tile germ line but not in the soma," Genes & Development (1990) 4(5):789-805.
Mattox et al., "Autoregulation of the splicing of transcripts from the transformer-2 gene of *Drosophila*," Genes & Development (1991) 5:786-796.
Matz et al., "Fluorescent proteins from nonbioluminescent Anthozoa species," Nat Biotechnol (1999) 17(10):969-973.
Maynard-Smith et al., "A directed approach for engineering conditional protein stability using biologically silent small molecules," J Biol Chem (2007) 282(34):24866-24872.
Miller et al., "A TALE nuclease architecture for efficient genome editing," Nat Biotechnol (2011) 29(2):143-148.
Miller., "An improved zinc-finger nuclease architecture for highly specific genome editing," Nat Biotechnol (2007) 25(7):778-785.
Mishra, "Understanding Forest Biology," Discovery publishing house (2009) 3 pages.

(56) References Cited

OTHER PUBLICATIONS

Morrison et al., "Genetic Improvements to the sterile insect technique for agricultural pests," Asia Pacific J MOI Biol and Biotechnol (2010) 18(2):275-295.
Morrison et al., "Engineered repressible lethality for controlling the pink bollworm, a lepidopteran pest of cotton," PLOS One (2012) 7(12):e50922.
Mounier et al., "Insect muscle actins differ distinctly from invertebrate and vertebrate cytoplasmic actins," J Mol Evol (1992) 34(5):406-415.
Munoz, et al., "The AeAct-4 gene is expressed in the developing flight muscles of female Aedes aegypti", Insect Molecular Biology, vol. 13, No. 5, Oct. 2004, pp. 563-568.
Namciu et al., "Human matrix attachment regions insulate transgene expression from chromosomal position effects in *Drosophila melanogaster*," Mol Cell Biol (1998) 18(4):2382-2391.
Nielsen et al., "Axoneme-specific beta-tubulin specialization: a conserved C-terminal motif specifies the central pair," Curr Biol (2001) 11(7):529-533.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
Nongthomba et al., "Expression and function of the *Drosophila* ACT88F actin isoform is not restricted to the indirect flight muscles," Journal of Muscle Research and Cell Motility (2001) 22:111-119.
O'Brochta et al., "Gene vector and transposable element behavior in mosquitos," J Exp Biol (2003) 206(Pt 21):3823-3834.
Ohshima et al., "Reassessment of 79B actin gene expression in the abdomen of adult *Drosophila melanogaster*," Insect Molecular Biology (1997) 6(3):227-231.
Osanai-Futahasi et al., "A visible dominant marker for insect transgenesis," Nature Communications (2012) 3:1295.
Osterwalder et al., "A conditional tissue-specific transgene expression system using inducible GAL4," Proc Natl Acad Sci (USA) (2001) 98(22):12596-12601.
Oxitec Nov. 2011 Newsletter, http://www.oxitec.com/our-news/newsletters/november-2011-newsletter/, downloaded Dec. 13, 2011, 6 pages.
Pane et al., Development (2002) 129:3715-3725.
Papathanos et al., "Sex separation strategies: past experience and new approaches," Malar J. (2009) 8 Supp 2:S5.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
Parker, "Mass-rearing for sterile insect release," The Netherlands, Springer (2005) pp. 209-232.
Peloquin et al., "Germ-line transformation of pink bollworm (Lepidoptera: gelechiidae) mediated by the piggyBac transposable element," Insect Mol Biol (2000) 9(3):323-333.
Perera et al., "Germ-line transformation of the South American malaria vector, *Anopheles albimanus*, with a piggyBac/EGFP transposon vector is routine and highly efficient," Insect Mol Biol (2002) 11(4):291-297.
Perezgasga et al., "Regulation of transcription of meiotic cell cycle and terminal differentiation genes by the testis-specific Zn-finger protein matotopetli," Development (2004) 131(8):1691-1702.
Perrin et al., "The actin gene family: function follows isoform," Cytoskeleton (2010) 67(10):630-634.
Phuc et al., "Late-acting dominant lethal genetic systems and mosquito control," BMC Biol (2007) 5:11.
PiggyBac website, http://piggybac.bio.nd.edu/, visited Mar. 21, 2006.
Pinkerton et al., "Green fluorescent protein as a genetic marker in transgenic Aedes aegypti," Insect Mol Biol (2000) 9(1):1-10.
Prasher et al., "Primary structure of the Aequorea victoria green-fluorescent protein," Gene (1992) 111(2):229-233.
Qin et al., "Systematic comparison of constitutive promoters and the Doxycycline-inducible promoter," PLOS One (2010) 5(5):e10611.
Raja et al., "Replacement by *Drosophila melanogaster* Protamines and Mst77F of Histones during Chromatin Condensation in Late Spermatids and Role of Sesame in the Removal of These Proteins from the Male Pronucleus," (2005) Mol Cell Biol 25(14):6165-6177.
Remy et al., "Zinc-finger nucleases: a powerful tool for genetic engineering of animals," Transgenic Res (2010) 19:363-371.
Rendon et al., "Medfly (Diptera: Tephritidae) genetic sexing: large-scale field comparison of males-only and bisexual sterile fly releases in Guatemala," J Econ Entomol (2004) 97(5):1547-1553.
Robinson et al., "Ceratitis capitata—a suitable case for genetic sexing," Genetica (1982) 58(3):229-237.
Robinson et al., "Prospects for the future development and application of the sterile insect technique," The Netherlands, Springer (2005) pp. 727-760.
Robinson, "Genetic Basis of the Sterile Insect Technique," in: Sterile Insect Technique, Principles and Practice in Area-Wide Integrated Pest Management, Dyck et al., (eds.), The Netherland, Springer (2005) pp. 95-114.
Robinson, Mutation Research (2002) 511:113-132.
Ronaldson et al., "Two independent cis-acting elements regulate the sex- and tissue-specific expression of yp3 in *Drosophila melanogaster*," Genet Res. (1995) 66(1):9-17.
Rong et al., "A targeted gene knockout in *Drosophila*," Genetics (2001) 157(3):1307-1312.
Rong et al., "Gene targeting by homologous recombination in *Drosophila*," Science (2000) 288(5473):2013-2018.
Rong et al., "Targeted mutagenesis by homologous recombination in *D. melanogaster*," Genes Dev (2002) 16:1568-1581.
Roper et al., "Contribution of sequence variation in *Drosophila* actins to their incorporation into actin-based structures in vivo," Journal of Cell Science (2005) 118:3937-3948.
Rossler, "The genetics of the Mediterranean fruit fly: a "white pupae" mutant," Annals of the Entomological Society of America (1979) 72:583-585.
Rubin et al., "Genetic transformation of *Drosophila* with transposable element vectors," Science (1982) 218(4570):348-353.
Russ et al., "Self-Deleting Retrovirus Vectors for Gene Therapy," Journal of Virology (1996) 70(8):4927-4932.
Saccone et al. (2000) "Sex Determination in Medfly: A Molecular Approach," In: Area-Wide Control of Fruit Flies and Other Pest Insects, Tan, K.H. ed., Penerbit USM, Penag, pp. 491-496.
Saccone et al., "Sex determination in flies, fruit flies and butterflies," Genetica (2002) 116:15-23.
Salvemini et al., "Genomic organization and splicing evolution of the doublesex gene, a *Drosophila* regulator of sexual differentiation, in the gengue and yellow fever mosquito *Aedes aegypti*," BMC Evolutionary Biology (2011) 11(1):41.
Santel et al., "The *Drosophila* don juan (dj) gene encodes a novel sperm specific protein component characterized by an unusual domain of a repetitive amino acid motif," Mech Dev (1997) 64(1-2):19-30.
Scali, et al., "Identification of sex-specific transcripts of the Anopheles gambiae doublesex gene", Journal of Experimental Biology, vol. 208, No. 19, Oct. 2005, pp. 3701-3709.
Schetelig et al., "Strategy for enhanced transgenic strain development for embryonic conditional lethality in Anastrepha suspensa," Pro Natl Acad Sci (USA) (2012) 24: 9348-9353.
Schwechheimer et al. (2000) "Transactivation of a Target Gene Through Feedforward Loop Activation in Plants," Funct Integr Genomics 1 :35-43.
Sepp et al., "Conversion of lacZ Enhancer Trap Lines to GAL4 Lines Using Targeted Transposition in *Drosophila melanogaster*," Genetics (1999) 151:1093-1101.
Shah et al., "Cardiac remodeling in *Drosophila* arises from changes in actin gene expression and from a contribution of lymph gland-like cells to the heart musculature," Mech Dev (2011) 128(3-4):222-233.
Shelton et al., "Field tests on managing resistance to Bt-engineered plants," Nature Biotechnology (2000) 18:339-342.

(56) References Cited

OTHER PUBLICATIONS

Shockett et al. (Jul. 1995) "A Modified Tetracycline-Regulated System Provides Autoregulatory, Inducible Gene Expression in Cultured Cells and Transgenic Mice," Proc. Nat. Acad. Sci. USA 92:6522-6526.
Simmons et al., "Field Performance of a Genetically Engineered Strain of Pink Bollworm," PLoS ONE (2011) 6(9):1-11.
Smith et al., "Testis-specific expression of the beta2 tubulin promoter of Aedes aegypti and its application as a genetic sex-separation marker," Insect Mol Biol (2007) 16(1):16-71.
Sondergaard et al., "Nutritional response in a Drosophila yolk protein gene promoter," Mol Gen Genet (1995) 248(1):25-32.
Spradling et al., "Transposition of cloned P elements into Drosophila germ line chromosomes," Science (1982) 218(4570):341-347.
Spradling et al., "P element-mediated transformation," Drosophila a practical approach (1986) Chapter 8:175-197.
Stadtfeld et al., "Without a trace? PiggyBac-ing toward pluripotency," Nat Methods (2009) 6(5):329-330.
Stebbins et al. (2001) "Adaptable Doxycycline-Regulated Gene Expression Systems for Drosophila," Gene 270: 103-111.
Stebbins et al. (2001) "Tetracycline-Inducible Systems for Drosophila," Proc. Nat. Acad. Sci. USA. 98:10775-10780.
Steiner et al., "Homologous recombination as the main mechanism for DNA integration and cause of rearrangements in the filamentous ascomycete Ashbya gossypii." Genetics (1995) 140:973-987.
Tamura et al., "Germline transformation of the silkworm Bombyx mori L. using a piggyBac transposon-derived vector," Nat Biotechnol (2000) 18(1):81-84.
Theodoraki et al., "cDNA cloning, heat shock regulation and developmental expression of the hsp83 gene in the Mediterranean fruit fly Ceratitis capitata," Insect Mol Biol (2006) 15(6):839-852.
Thomas et al., "Insect population control using a dominant, repressible, lethal genetic system," Science (2000) 287(5462):2474-2476.
Timoshevskiy et al., "An intergrated linkage, chromosome, and Genome map for the Yellow Fever Mosquito Aedes aegypti," PLOS Negected Tropical Diseases (2013) 7(2):e2052.
Timoshevskiy et al., "Genomic composition and evolution of Aedes aegypti chromosomes revealed by the analysis of physically mapped supercontigs," BMC Biology (2014) 12(1):27.
Urnov et al., "Highly efficient endogenous human gene correction using designed zinc-finger nucleases," Nature (2005) 435:646-651.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Viktorinova et al., "Comparative analysis of binary expression systems for directed gene expression in transgenic insects," Insect Biochem Mol Biol (2007) 37:246-254.
Vishvanath et al., "Genome sequence of Aedes aegypti, a major arbovirus vector," Science (2007) 316(5832):1718-1723.
Vivinus et al., Eur. J. Biochem. (2001) 268:1908-1917.
Vulsteke et al., "Properties and phosphorylation sites of baculovirus-expressed nuclear inhibitor of protein phosphatase-1 (NIPP-1)," J Biol Chem (1997) 272(52):32972-32978.
Webster et al., Cell (1988) 52:169-178.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the Drosophila slit and Toll genes," Mech Dev (1993) 40(3):141-154.
White-Cooper et al., "Transcription of meiotic cell cycle and terminal differentiation genes depends on a conserved chromatin associated protein, whose nuclear localisation is regulated," Development (2000) 127:5463-5473.
Wilson et al., "Position effects on eukaryotic gene expression," Annu Rev Cell Biol (1990) 6:679-714.
Wilson et al., "Sperm plasma membrane breakdown during Drosophila fertilization requires sneaky, an acrosomal membrane protein," Development (2006) 133(24):4871-4879.
Wimmer, "Eco-friendly insect management," Nat Biotechnology (2005) 23(4):432-433.
Windbichler et al., "A synthetic homing endonuclease-based gene drive system in the human malaria mosquito," Nature (2011) 473(7346):212-215.
Windbichler et al., "Homing endonuclease mediated gene targeting in Anopheles gambiae cells and embryos," Nucleic Acids Res (2007) 35:5922-5933.
Windbichler et al., "Targeting the X chromosome during spermatogenesis induces Y chromosome transmission ratio distortion and early dominant embryo lethality in Anopheles gambiae," PLoS Genet (2008) 4(12):e1000291.
Wise De Valdez et al., "Genetic elimination of dengue vector mosquitoes," Proc Natl Acad Sci USA (2011) 108(12):4772-4775.
Wobus et al., "A New Transposable Element in Chironomus thummi," Mol. Gen. Genet. (1990) 222:311-316.
Woltjen et al., "piggyBac transposition reprograms fibroblasts to induced pluripotent stem cells," Nature (2009) 458(7239):766-770.
Wool et al., "Genetically-Induced Susceptibility to Malathion in Tribolium castaneum Despite Selection for Resistance," Ent. Exp. & Appl. (1980) 183-190.
Written Opinion for PCT/GB2007/000488, dated Jun. 6, 2007, 8 pages.
Written Opinion for PCT/GB2004/002021, dated Oct. 4, 2004, 5 pages.
Written Opinion for PCT/GB2004/002869, dated Jan. 12, 2005, 8 pages.
Written Opinion for PCT/GB2004/003263, dated Nov. 5, 2004, 5 pages.
Wu et al. (Jun. 2000) "Expression of Highly Controllable Genes in Insect Cells Using a Modified Tetracycline-Regulated Gene Expression System," J. Biotechnol. 80(1):75-83.
Zhao et al., "Male germ cell specification and differentiation," Dev Cell (2002) 2(5):537-547.
Zimowska et al., "The beta2-tubulin gene from three tephritid fruit fly species and use of its promoter for sperm marking," Insect Biochem Mol Biol (2009) 39(8):508-515.
International Search Report and Written Opinion for PCT/IB2017/001128, dated Dec. 13, 2017, 17 pages.

gaccctttgtgccccctgcatattttgatttattttaagctgaactagttctacattttcaaacttagcgcagctcatacatgtac
atatctatatatgtaagtatgtatgtatatacgttcgtgtgcatgtgcagtgtgcatgcactgtgcgcaataaaacctgctgg
aactcatttacaaagcaaaaaattattctttcccatcgattacagcattaaaatcagcgtaagtatgtaaacacgcccca
tttaagaatccaaaaatacttgcactccatttccatagtgcagccaaatgcatggctatttgtgtgtatttaatgtatgcatat
atgttcgtatatttgtatgtatgaatttatgactttatattcaactccactaaaaattgcttttcaccattcggtgggtattcacac
attttttacatatatttcatatatcaacgctccagaaatgccgcttgttttactccaaaaggatgcggtgtgccggaaattaa
gaaatcctgctgtccagccaatttatgtatgccactggaacggcaataacgcgtggccatgtaaacaaatgtgggatc
aacaagcaaaacgctggccaagcaaagaaattggttagagaacaaaaataaaaagaaacaagcaattcgaaa
gctatcatctcaacaacaattacagcaacaatacgagcaaagcgcgcagatcaaagtggcagcacctcgaaaaat
ccacagaggtggcaacatggagatgaccaaaaatagaaatgtttaacacacagaaaaaggcgccaacaacaaa
acaacgtcataaagtattcaacgaaggtgctgagcgcctctacatgcacgtacatacacacaaaaacataaaaattc
ctacattatgatacatacatacatacataggtgcttacaagtgtacctacatatttattagtatccaatacatacaaatgca
aatttagataccagtgcgtgggggccgccacagctgagcgagagcaatacgcaatgtgagagcaccagcaaccg
aaaatatatatttaataaacatatttgaaaaattaaatgttcgaaaatagaatattcaaaatatatttgtttgaaaagcga
caaaatgatcaccgtccggatctattgaagcgcctgacaatgcgtgcaaaagggatagcgattgcgtcagtatgcgc
ggcaataaacctcaaacacttcatatctctccctccacacacaacccgaaaagatcgcgcgaagcaagacgagga
attcaacaaacaatagcaacaacacatctgcaatgcttgtatattgaatataaatttgttaaagaaatttcgtgcgcaccc
caccacagcatccccattatggtgagcgcttaatagcagccgacataacgttgacgcggcagccttgccttatacggc
gctttggagcgcttttagtggggagccgtaccaattgccatggaatatatatatttgtatgtatgtatgtatgtatgcacaaa
caaacccgatgatgccgaactaaacgcgagcaatctgtgagatcagcgaacagcgagcagcgaataacgagcg
aaccacccaacaaagtgattatgatcattgctgtgacgctatgacgccacggctcgcttcgttcgtgggctgagtgggg
tgcttcagtgcgcaggagcacgatcgttgttgctgactcgctcggatgcgcgcacatcgttttccatgcagctcaacatta
acgtgtgggtgtgtatgcgtatatacggcatatgacgatgagcgcggtgtgatgggtctattttagtggcgttgaaaaat
cgtaaacacaacgaatccctctttgatgtgaacgtattggtgttgccgctattatctgtcattgtatcagtggatcggtgtatc
ggtgttttcgtgttggcggtggaggtgagacatttgttggagcgttgcgggtgtgtggggacgtgaagcgacgtgaatgc
ctaatgttggctattgccgaagaatttttggatttgttaagtgatcaacatgaaaagtgtagttttaagttgattggtataaaa
tcggctggtagtagccaaggcactttagtcagtcagttgtgttccaaagcgttcagaacacattgccatatttctttacttatt
tcttcttgctcgtggttaaaaaacacaaaactcagacaaaatgtgtgacgatgaggttgctgctttggtcgttgataatggt
ccggt Fig. 1. Sequence of the Mexfly Muscle actin promoter and 5'UTR region used in construct #4014 (SEQ ID NO: 1).

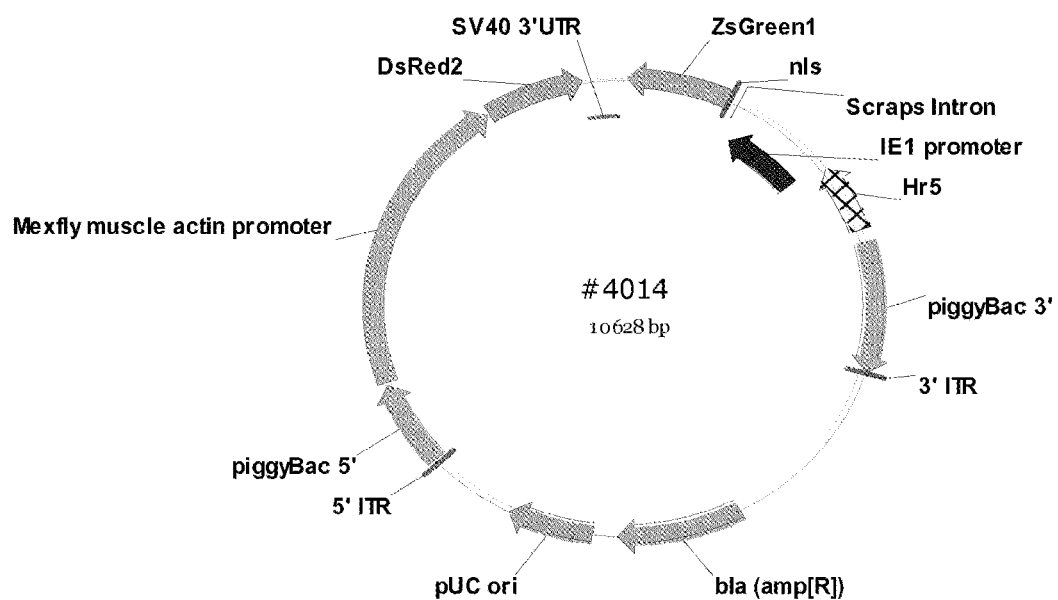
Fig 2. #4014 PB Hr5IE1-Zsgreen-MexMuAcpro-Dsred gccataggacatgacactgtggaagtaactaaagtaaactaaacgagccgtgtccgcatttgttaacattctaatttttttt
actgcgtatgctgcagagctaagcttactcgccaatttatgaatatgaggtccccactgcagtttggagtccactgttata
ccaagaaatacggttgactcaacaagctccaatgattcctcagaaacaattacattactatctacttgtctcacatttaaa
gatgatttaatacattttaaagtaaatttaatacatttcgttattatttaattttaacgttattttttaatttaatacattgcggcatca
caatttattgcttacgtttccattgataaataaaccgtaatgtatgagtagtattgtcgattgcatcgttcaatgcgcagatcg
cctgctagcggtattggcatgcaatcggatcaatgaatcaattgcaggtcacagggcggttaaatttaactcgacttgtc
accggctaactgcatccgtggtgaagttcaatgtttgttttgatactaaatccgtttgttatgttcattacttaaactccatatct
atatattaataggtgaaggaaaaactttgtaccccttttttacgaaaattgcgcggacggatgagtatgaaatttctcacac
ttaaagagaatatagagaaggagtgcacaatgctaatatatttttaaatattcgataaaagatactttaaatcaataaag
aaacaattacacgcactaccatgtagttgacacacacacatataatactctttgtttattgcactgaagtattgtcaaacttt
tgttattgcttaaagtctgtagtcaaattgagaataggttagtattgtttatctttaatattacgagtattttctatagtgtagtctt
ggcgaaatctgtaacaataggaccataataatgttgaaacttataattcaattaattatagtcgaatttcgactactgcag
gaccactagtataaataattatatgaaaataaattaacatgatccattattacgagaaaaacacacacactacatgatg
ctaagtaaagcttagaaatgccgtcacccattttgagagctaacgtggttgacatctccgcggctctacagcccacctg
acgcgggctctcctgtcgcgactctacgatggcgtggagacggtaaccgcttacggtggtgagttagttaagtttgcca
acgacgacaatcaacattttcagataaagaaacatatgtacttgcagtaaagtaaagttatacattcgatgcgatttgaa
cacatgtaaacatgtaacaaaaagtaggatgttttttgactggcccgcagctcccgtgggactaagctgttactttgaga
catgaggtcaatgtctgaattgtatgatacagtttacaggctccctcactcctcaaatacggatgcatgttatgtatacgag
acctttaaaaatttccgtaactactgtagatagagtgttctgaacacacgctgacaggcaggaatcctacctacttcagc
ccccccagggttcatgggttctggcttaacattagatgtgccacctgcacaccgttctatttaaactgaaaaataaaatttta
ggcgaacgacaccatccagtgaaatgatttgcaataagcacttcttatatgccacgttactgtacatcatatatttttaccc
cacatcagggttaactctacataggtacataatatcactacatagtataaaacagagtcgctttctctgtccctatatccct
atgtatgcttaaatctttaaaactacgcaacggattttatgcggttgtttataatagatagagtgattgaagagcaaggttt
atatgtataataacatccattaaatagtggagaaatcaataataaattacagtttccgaagcgaagcgagggcggatc
gctagtaatattattatttttttgctggaaactatgcgtgtttttcaaataatatatatttcttttgggttgttaccaactccaatta
catatcaggcgtcattaaaaaatactacggaattttgtggtctgaataatatgtaggtattgatattaagcattggtcatgtt
gtctgattttaatgcttttattttatttataatgtattgaattcttagttattatcagtttgaagaattacaaaagtcaaatacctaa
ataaaatctatatttttttattcgcattgtacatatttctgaactctaagtacggtcgagcgcggcgcccatcgcccgcaatg
gctcgcggcgcgctcaaatcttttcgcgatttaatctgtttttaaccaattttcggtgcaaaatattattgaacaataatccaa
atctgttatttatttatacagtaagttcgttagacaggtaagttagtgtaattgtgtacatttcgcgtgtattatcgaacgcgatc
gtggagaggcggggcgacccggctcgccttgtatggagcgcggccgcggctcacgcgcgtcctatataagaaac
cggcgccgggaaccgccgcactcgcagtcc Figure 3 DNA sequence of the Bombyx mori muscle actin promoter (BmA1) fragment (SEQ ID NO: 5)

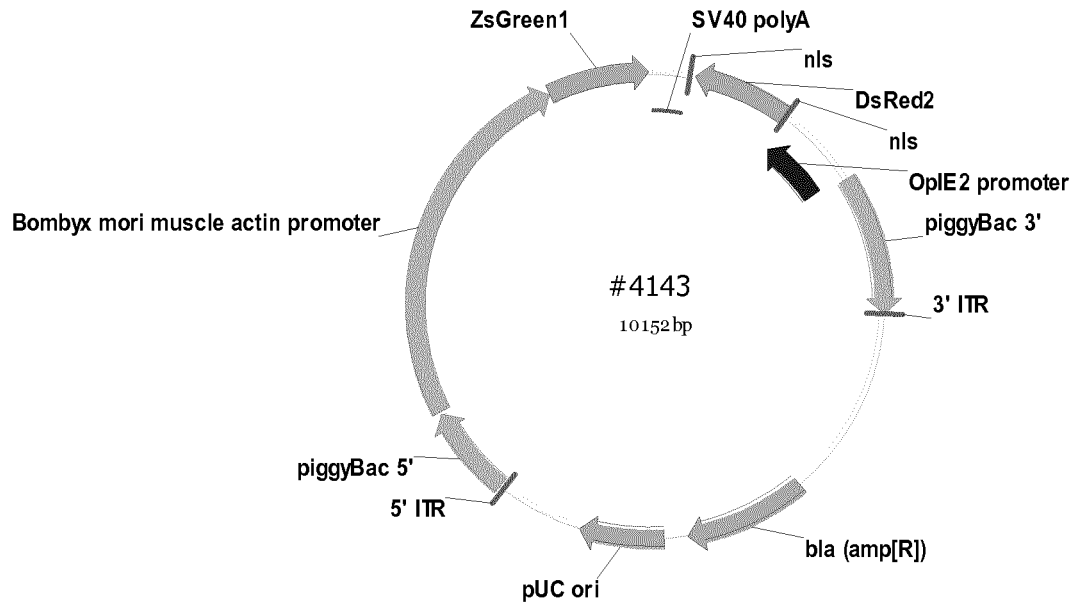
Figure 4 Plasmid map of #4143
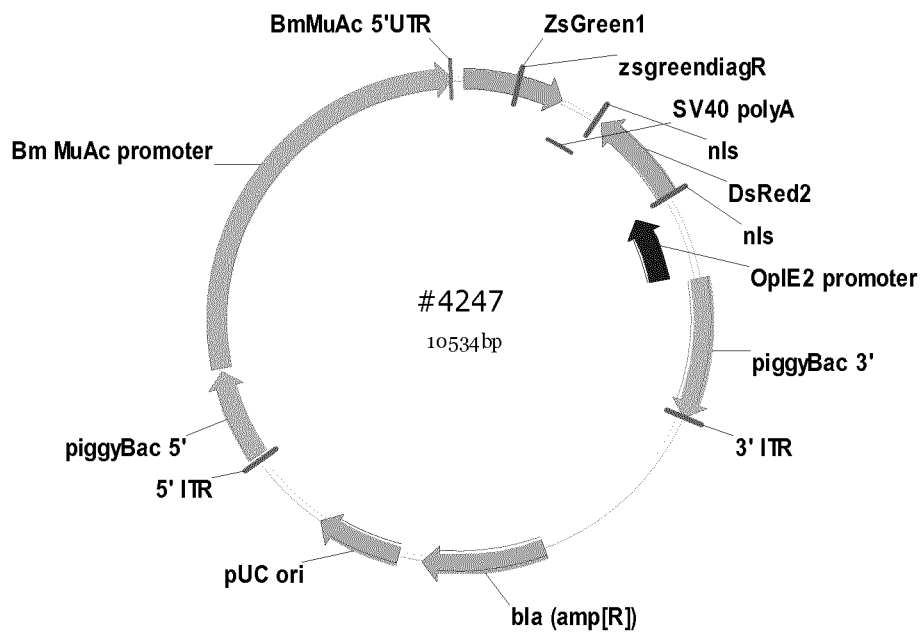
Figure 5 Plasmid map of #4247

```
gttcgagcagtagacccaccaaccatagaagtgattaaagaggctgttagtcagctgaagaactgcagctgggaag
gacgagatccctgtcaaacttctcaaacacgaaagtcctccgagtatttctgaaggtataggagggcgaagaaatgc
ccaccggctggtttgaagaaaaaacacagactggagtgcaacaattacaaaaggataacagtgctcaattcagcgt
acaaaatactgtcgggcatcttgtcgaatagattgctcgaggagttaatcgtcgacgaataccacgctggttttgtgag
ggctgctcgacaacggaccagatgtttaccttacgaatgaccttagataacatccaggagtttagcttgcagagtcacc
atctgtttattgatttcaaggcggcgcacgattcaatgagaagaaatgagctgtggcagataatgtctgaacatggttttc
cgacgaaattgatcaggctgatacgtgcaacatgctccttggctttgcggacgatatggaccttattggaatcggtcgaa
gatcagcgaaggaggccttcgtgcatcttgagagggagacggattggccttactattaattctacccaaacaacaaat
atggtagatagaggtaggcctagtggtgctggtactgaggtaatctttgatggggatgtgtttgaagttatcgaagatttag
ttatttcgaagcacttgtgacatgtgacaatgacgtttctcgcgaaataaaaagacgtgttggggctgcgaatagggcg
ttttacggactacgtaaccaacttaagtcctgcaacttgcaaacggaaacaaaattcatcctgtatgaaacaatgattcg
cccgatggctctcctcgggcacaaagcacggacattgaaagaagcagaccgacacttacaggtcaaatacatctat
gcaacagaacttgattctcaacttatgagcactttcatagttataaaaattgagagcttcttcatcaactaacaattttcgc
atgtgtatgttgctctggaaagtcgagtaaatttccaattcgaaaaaattctcgaccggtgggattcgaacccacgagcc
tttccttggtcttgctgaatagctgtgaacggtgaacgcaccgctacagctatttgcacttttctcgttttttttttttcaaaatccc
aatgaaaatccttcaaaatgttgcacttcaattttgtacgttctttgctcatgatgtaaatttcatttgatttaatcactaatttatt
gcttccaacatgagcaattttcgataaaaatgtattccggaaacatgttcgcaatacttgtcgcacaactaagaaaagt
aacaggtgaaacattctctaatgatgctttcttgcgcgtgtgacgtcgcgacgacgacggcggcggttcttctaaccgttt
ttggcaaaccgtcacgtcctgaaaagcggctacccagtcacgcagcgcggcggaggcaaaggtaaaacactaca
gctcggtcagggatgagtaaggacgagataaattaaaaatatgagaaattcgtctcccagtcatgtttattttagctcga
aagtgagcgattccttccccgcgtggctgcgtcgtgttttgttgtgatcaattccaagtttgggatcacgggaagagcgag
agagaaagagttcgcgagaatttcagcaccaaattggtattagatagtgtcatgtgcaccgtatataaactttgagccc
aaccgcca
```

Figure 6 Aedes aegypti muscle actin promoter fragment (SEQ ID NO: 6)

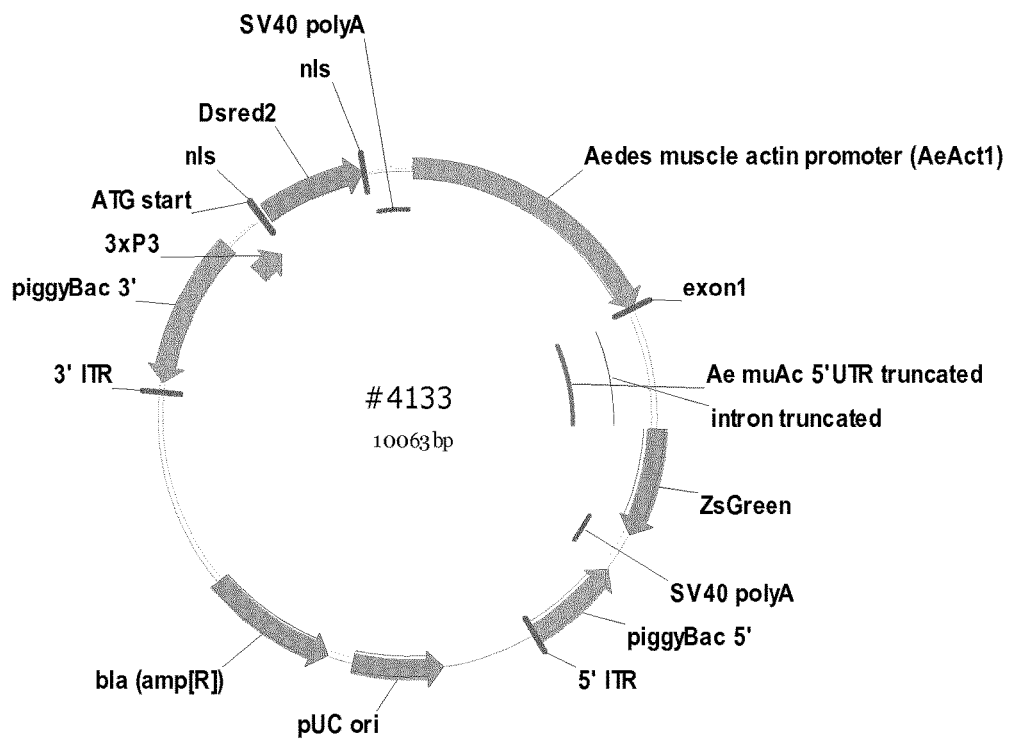

Figure 7 Plasmid map of #4133

CGGCATTCATTCTAGTTCCGAAACCGTTTGCCGTGC*cacgtgt*tcgcgatcgttctcattcgatc
ggagtgactgccgtttgaggattagtgtgtgcagaagaaaccaacggatagaagttccttttttgtgtgagtgtcattggcc
tttgatggataattaatgtggaaatgattggatatggtgtactaactgcattgaataaaatattacataatgtgagaaaga
ctcgaacaatgtaaattacgaaaatgaaaattgcaaagatgaaacagttgaacgcttgaatgaagagtacgtggagt
gattcaacaatgcaatatttaacattgaacaaatctacaaaagtgaataatacgttaaaaaaaataagaatgcaatgg
acgatttggttgaagtttgacaaacaacatcaaatcggcagggcttcctaaggcatagcatgccgtatatcgagtggca
agctcgaagataccatatgctctggaaagtcgataaaatttcctactagaaaagatcctcggctcgtgggattcgaatc
cacgaccctcagcttcataaagaattcttattttatacacaatgaagtaaaatttgtgtgcatacttcaaaattgtctttgaa
gtgtagttagtcattccaacgttatcatattgtaatattatttatactaatctttaaagcacaaataccatggtccatatcgga
aattggcatacatatggcatatgatataatgccactaggttcctaacaagggaattgtactatgcgaatagacggttgG
CTAGCAT Figure 8 5'UTR (including truncated intron in lower case) of #4133 (SEQ ID NO: 17)

atggcccagtccaagcacggcctgaccaaggagatgaccatgaagtaccgcatggagggctgcgtggacggcca
caagttcgtgatcaccggcgagggcatcggctacccctcaagggcaagcaggccatcaacctgtgcgtggtggag
ggcggcccccttgcccttcgccgaggacatcttgtccgccgccttcatgtacggcaaccgcgtgttcaccgagtaccccc
aggacatcgtcgactacttcaagaactcctgccccgccggctacacctgggaccgctccttcctgttcgaggacggcg
ccgtgtgcatctgcaacgccgacatcaccgtgagcgtggaggagaactgcatgtaccacgagtccaagttctacggc
gtgaacttccccgccgacggccccgtgatgaagaagatgaccgacaactgggagccctcctgcgagaagatcatc
cccgtgcccaagcagggcatcttgaagggcgacgtgagcatgtacctgctgctgaaggacggtggccgcttgcgctg
ccagttcgacaccgtgtacaaggccaagtccgtgccccgcaagatgcccgactggcacttcatccagcacaagctg
acccgcgaggaccgcagcgacgccaagaaccagaagtggcacctgaccgagcacgccatcgcctccggctccg
ccttgccctccggactc Figure 9 DNA sequence of ZsGreen of #4133 (SEQ ID NO: 18)

atggcctcctccgagaacgtcatcaccgagttcatgcgcttcaaggtgcgcatggagggcaccgtgaacggccacg
agttcgagatcgagggcgagggcgagggccgcccctacgagggccacaacaccgtgaagctgaaggtgaccaa
gggcggccccctgcccttcgcctgggacatcctgtcccccagttccagtacggctccaaggtgtacgtgaagcaccc
cgccgacatccccgactacaagaagctgtccttccccgagggcttcaagtgggagcgcgtgatgaacttcgaggac
ggcggcgtggcgaccgtgacccaggactcctccctgcaggacggctgcttcatctacaaggtgaagttcatcggcgt
gaacttcccctccgacggccccgtgatgcagaagaagaccatgggctgggaggcctccaccgagcgcctgtaccc
ccgcgacggcgtgctgaagggcgagacccacaaggccctgaagctgaaggacggcggccactacctggtggagt
tcaagtccatctacatggccaagaagcccgtgcagctgcccggctactactacgtggacgccaagctggacatcacc
tcccacaacgaggactacaccatcgtggagcagtacgagcgcaccgagggccgccaccacctgttcctg Figure 10 DNA sequence of DsRed2 of #4014 (SEQ ID NO: 19)

taagatacattgatgagtttggacaaaccacaactagaatgcagtgaaaaaaatgctttatttgtgaaatttgtgatgcta
ttgctttatttgtaaccattataagctgcaataaacaagttaacaacaacaattgcattcattttatgtttcaggttcaggggg
aggtgtgggaggttttttaaagcaagtaaaacctctacaaatgtggtatggctgattatgatc Figure 11 Sv40 3' UTR Sequence (SEQ ID NO: 20)

gtcttttgattgtgaaagatggtgaaatgcgttgatgcaaacatatgccaacaacaacagcagcagcaacatcaaca
ataacaacaactctgcaaatagccagcacaactgctcagacttcgtgcaacgaacaccaataaccagcataacaa
ataccactacgcattcgagaactgcaattacaacaacaaaagaggcattaatagcaacaacaaaaatgagagtgc
atgctaattccaacaaaagcaaaaactacagatatcaacaaggtaatgagaattcaacaaatgcaataaatggcgc
ttccagtagcgaaagagaaggacacaaaaacaaaaccaaatatataaagaaagcaatctctgaggaaatgccca
tgagcgccatctagcaattgaatcgctttacgttgcatttgcatgtgaacatttttaattatatttctttttctggattttatacaat
aaaatgcgtgtaaaactgaaatttataaatttaactaacagaatatcaaaggaaaattatgaaaatgtagaaaaaaat
tattaaaaattactaaaatccaaacaaatgaacatcaaataattcactaataagagctaattaagtaaacatctttccatt
gactaaccaaggcaaaaatactaaaagtaaa Figure 12 Mexfly Muscle Actin 3' UTR sequence (SEQ ID NO: 21)

INSECT MUSCLE ACTIN PROMOTER

CROSS-REFERENCE TO RELATED APPLICATIONS

This application is a continuation of U.S. patent application Ser. No. 14/773,252, filed Sep. 4, 2015, which is a U.S. National Stage Application of International Application No. PCT/EP2014/054290, filed Mar. 5, 2014, which claims the priority benefit of GB 1303932.6, filed Mar. 5, 2013. The contents of the above-listed applications are incorporated herein by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750402000201SeqList.txt, date recorded: Jun. 23, 2017, size: 15,410 bytes).

FIELD OF THE INVENTION

The present invention relates to expression systems comprising a muscle actin promoter suitable for expression in insects.

BACKGROUND TO THE INVENTION

Sterile Insect Technique (SIT) (Dyck et al., 2005; Knipling, 1955) involves mass rearing and release of sterile insects in a given area. Sterile insects mate with their wild counterparts leading to a decrease in the wild population. SIT can be used to control the population of pests. Pests are detrimental to humans or human concerns such as agriculture or livestock production. Pests are often disease vectors, or simply put, they carry and spread disease. Examples of such pests include mosquitos of the genus *Aedes*, principally *Aedes aegypti*, which can spread the dengue virus, causing dengue fever, or the yellow fever virus causing yellow fever. *Anopoheles* mosquitos are responsible for spreading malaria. However, despite its environmental benefits, SIT has been used successfully for only a limited number of insect pests to date.

Modern genetics can provide significant advances in current SIT programmes and may help in implementing pest management programmes that otherwise would not be possible. These advances include: a) improving the identification of released individuals, b) removing the need for radiation-sterilisation and c) providing automated sex-separation prior to release to eliminate females from the release population ("genetic sexing") (Alphey et al., 2008; Papathanos et al., 2009).

Female lethal RIDL technology (female-specific Release of Insects carrying a Dominant Lethal, fsRIDL) is highly effective in separating sexes and has been successfully tested in laboratory, greenhouse and semi-field experiments (WO 01/39599). The present application and our work on genetic male sterility (GB2500113 and WO2013/131920) provide resourceful additions to the current RIDL system but more importantly, they effectively and sustainably address the two remaining genetic advances (a) and b) respectively) discussed above.

It is essential to be able to detect the presence of wild insects, even amongst overwhelming numbers of released sterile insects. This requires the released insects to be marked in some way, to distinguish them from wild type insects. Current marking techniques (Hagler and Jackson, 2001; Parker, 2005) mainly involve the use of coloured dyes in the larval diet that remains visible in the adults' tissues (e.g. codling moth, pink bollworm), or application of powder directly to the pupae (medfly). Although widely used, for example the Calco Red dietary dye for pink bollworm (*Pectinophora gossypiella*) moths (Graham and Mangum, 1971) and fluorescent powders marking the heads of adult medfly (Steiner, 1967), their application increases the cost of rearing, can increase the amount of handling required, and is prone to errors of interpretation (Hagler and Jackson, 2001; Hagler and Miller, 2002; Morrison et al., 2011; Robinson and Hendrichs, 2005).

It is also possible that a fraction of released sterile insects will lose the marker after release (Hagler and Jackson, 2001; Hagler and Miller, 2002), which would mean that on recapture they may be counted among the wild and fertile insects in the traps. Such error would not have a significant impact where large numbers of wild insects are captured, but in programmes attempting to eradicate a pest and where the wild pest is relatively infrequently captured, the presence of one such insect might provoke a costly round of quarantine and exceptional interventions. Furthermore, there are health concerns related to the effects of the powder on workers in mass-rearing facilities.

An example of a naturally occurring mutation that has been used as a genetic marker in operational SIT programmes is the white pupae (wp) mutation. It was first used in a small SIT trial in 1972-1973 against the Australian sheep blowfly (*Lucille cuprina*) as a sex separation mechanism (Robinson, 2002) through male-linked chromosomal translocations.

Following the successful sex separation of blowfly pupae based on pupal colour, the first medfly genetic sexing strains were constructed in 1984 by combining Y-autosome translocations developed by Robinson and van Heemert (1982) with the white pupae mutation (wp, located on chromosome 5) previously detected by Rössler (1979). However, these strains showed significant levels of genetic instability, which increased over time. As a result, some females could not be distinguished from the males and, consequently, an increasing number of females were released into the field (Franz, 2002).

Genetic markers that result in a new phenotype can be useful, but these markers are recessive and therefore apparent only when an individual carries two copies of the allele; they are, therefore, not applicable in situations where released males mate with the native wild female pest population and the progeny is being monitored. Furthermore, for monitoring purposes, the marker must be visible in adults and more importantly it must also be apparent in insects caught in traps, which might have been dead for several weeks before being examined.

Species-specific markers can be generated by isolating visible mutations in the species of interest, cloning the corresponding gene, and then rescuing the mutant phenotype by incorporating a wild-type copy of the gene through transformation. In fact the very first germ-line transformation of an insect; *D. melanogaster* (Rubin and Spradling, 1982) was possible due in large part to the availability of easily detectable eye colour markers that are the wild-type genes for mutated alleles affecting eye pigmentation. The first non-drosophilid transformation also took advantage of available eye colour markers. Loukeris et al. (Loukeris et al., 1995) identified Medfly transformants as phenotypic revertants of a white-eyed mutation carried by the recipient strain.

However, this procedure is laborious and requires manipulation for each species separately, thus is not cost-effective. Moreover, phenotypic mutations have not been identified for all pest insects of interest, a fact that limits the potential use of an SIT approach to pest control.

Germline transformation requires a selectable marker. Fluorescent proteins have been used for this purpose in the vast majority of transgenesis work on pest insects. Expression of these proteins, under the control of a suitable regulatory sequence, provides a readily distinguishable marker for the transgenic insect. From a SIT perspective, another key feature is that such markers are in-built and heritable (Alphey et al., 2008). For some species, full sterilisation by irradiation is achieved at a dose that compromises the performance of insects (Bakri et al., 2005). In SIT programmes against these species the preferred applied dose is not fully sterilising in order to minimise this effect, resulting in some fertile or partially fertile insects being released. The fact that dye or powder markers are not heritable leads to the possibility that recaptured progeny of such 'sterile' insects with wild counterparts will be scored as wild.

Examples of dominant, heritable fluorescent markers conferred through transgenesis can be found in Allen et al., 2004; Allen et al., 2001; Berghammer et al., 1999; Catteruccia et al., 2005; Catteruccia et al., 2000; Fraser, 2012; Handler and Harrell, 2001; Horn et al., 2002; Koukidou et al., 2006; Morrison et al., 2011; Peloquin et al., 2000; Perera et al., 2002; Pinkerton et al., 2000; Tamura et al., 2000). Fluorescent proteins that are widely used today as transformation markers and can be subsequently used as monitoring tools for the released insects in an SIT control programme, include the jellyfish GFP (Chalfie et al., 1994; Prasher et al., 1992), variants of this gene that result in enhanced green intensities and other colours (e.g., EGFP, cyan, yellow), and the coral, Discosoma striata, red fluorescent protein (DsRed or RFP) (Matz et al., 1999).

Although variable between insects, broadly speaking, the life cycle stages of insects are egg to larva to pupa to adult. Strong expression of any fluorescent marker, at all developmental stages, but mainly at the adult stage, is highly desirable for the rationale of reliably tracking the released insects in the field. Moreover, it is desirable that expression is widespread across all body segments of an insect (the head, thorax and abdomen). Although a stably expressed fluorescent protein will naturally undergo the same degeneration process as any other protein following an insect's death in a monitoring trap, for instance, data indicates that initial stronger fluorescent expression will lead to enhanced sustainability of the fluorescence phenotype.

A generic promoter that drives expression of a fluorescent protein should lead to ubiquitous tissue expression, therefore being readily visible under the appropriate excitation filters and presumably at all developmental stages. We have used such generic promoter-enhancer sequences with success in the past; for example, ie1-hr5, from baculovirus AcNPV which gives strong expression in *Ceratitis capitata* (Gong et al., 2005), *Anastrepha ludens* (Condon et al., 2007), *Bactrocera oleae* (Ant et al., 2012), *Aedes aegypti* (Fu et al, 2007), *Aedes albopictus* (Labbe et al, 2012), *Pectinophora gossypiella* (Li et al, 2012) and *Plutella xylostella* (Li et al, 2012). Unambiguous marker expression in insects has been also reported using the *Drosophila melanogaster* polyubiquitin promoter driving expression of the GFP (Green Fluorescent Protein) in *Drosophila melanogaster* and *Anastrepha suspensa* (Handler and Harrell, 2001; Handler and Harrell, 1999). Polyubiquitin is a highly conserved gene found in most organisms and is active in all cells. However, in many insects (especially Medfly), it gives only weak or diffuse fluorescence, and if the strength was to be increased, may result in toxicity.

An artificial promoter containing three binding sites for Pax-6 homodimers in front of a TATA box (3xP3) has also been used with success as a driver for an enhanced GFP variant (EGFP) expression in the eye of the fruit fly *Drosophila melanogaster* and in the flour beetle *Tribolium castaneum* (Berghammer et al., 1999) and other insects. It expresses most strongly from the brain, eyes, and ocelli in adults but transgenic animals were also identified as larvae and pupae. However, the restricted spatial expression of this marker makes it potentially ineffective for field monitoring purposes, as trapped insects may lose significant parts of their bodies in a trap, resulting in misidentification and mis-recording of the caught insects in a control programme. Pinkerton et al. (Pinkerton et al., 2000) have reported the use of EGFP under the control of the Actin5C promoter of *Drosophila melanogaster* as a genetic marker for the transformation of *Aedes aegypti* mosquitoes. Actin5C is a cytoplasmic actin which, like polyubiquitin, is expressed in all or most cells. EGFP expression was clearly visible in embryos and larvae. Strongest expression in late-stage embryos was seen in sections of the gut, a result that was expected when using the exon 1 proximal promoter of the actin5C gene (Burn et al., 1989). Expression of EGFP was also very clear in pupae, consistent with an increase in cell division during this life stage. Expression levels in adults varied from strong throughout the entire animal to lines where fluorescence was limited to the gonads. These differences are indicative of position effects between the different lines with the expression of the transgene being reduced except in those tissues in which there is a high level of cell division. This is potentially limiting for the use of this promoter as a monitoring tool and advocates the development of a substantial number of strains.

Tamura et al. (2000) investigated the feasibility of the GAL4/UAS system in conjunction with piggyBac vector-mediated germ-line transformation for targeted gene expression. *B. mori* cytoplasmic actin A3 (BmA3) was used to drive the GAL4 gene, GFP was used as the reporter. The same authors showed that the expression of the GFP was much higher using the GAL4/UAS system than the GFP expression obtained with BmA3 alone.

Concerns have been raised regarding the use of such markers in the field due to the potential fitness penalties they may induce in the recipient strain (Catteruccia et al., 2003; Irvin et al., 2004).

Accordingly, it is highly desirable to use a promoter that, on the one hand, is able to drive strong expression of a fluorescent protein (at most developmental stages) while, on the other, simultaneously poses only minimal, or no, deleterious effects to the general health and well-being of the insect strain (i.e. conferring no or little fitness disadvantage). Identification of such a promoter sequence has been challenging as evidenced by the failures seen in the prior art to date. A genetic strain comprising an expression system with such a promoter will also overcome the problems associated with current methods of insect identification using dyes and powders which are hazardous to workers and also prone to misidentification.

We have now, surprisingly, discovered that an expression system comprising a promoter that, in combination with a functional protein, such as a fluorescent marker, is both tissue specific and not generally limited to a given body segment, seems to confer no apparent fitness disadvantage on insect strains transformed with the system. Moreover, the promoter overcomes the disadvantages of existing methods that use dyes and powders to monitor insects. The disadvantages overcome or ameliorated by the present system include one or more of increased cost of rearing, increased amount of handling, errors in identification due to human error or loss of marker by the insect, and health concerns related to the effects of the powders on workers in mass rearing facilities. Furthermore, as the markers are non-heritable, re-captured progeny will be counted as wild-type.

SUMMARY OF THE INVENTION

Surprisingly, expression of marker proteins, such as fluorescent proteins, under the control of a muscle actin promoter has been found to be so strong that transgenic individuals are easily recognizable to the naked eye at all larval, pupal and, in some cases, adult stages.

Surprisingly, a further advantage is that, despite the strong expression of the marker protein, such as a fluorescent protein, no adverse effects of the transgene were observed in any of the transgenic strains.

Thus, in a first aspect, the present invention provides a gene expression system, suitable for expression in an insect, comprising an insect muscle actin promoter operably linked to a marker gene.

The marker gene preferably encodes a fluorescent protein.

It is preferable that the muscle actin promoter is from Mexfly. In the alternative, it is preferable that the muscle actin promoter is from *Aedes aegypti* or *Bombyx mori*. Preferably, the muscle actin promoter comprises SEQ ID NOS: 1, 5 or 6. The muscle actin promoter, most preferably from Mexfly, *Aedes aegypti*, or *Bombyx mori*, may be used in any insect, most preferably insects of the order Diptera or Lepidoptera. Further preferred examples are provided below. In one embodiment, it is preferred that promoter is from a member of the same family that the target insect (insect of interest) belongs to: e.g. *Bombyx mori* muscle actin in pink bollworm; or Medfly muscle actin in another Tephritid, for example.

In one embodiment, it is preferable that a gene expression system of the invention is capable of expression in insects of the order Diptera. In another embodiment, it is preferable that a system is capable of expression in the order Lepidoptera. Other preferred orders in which it systems of the present invention are preferred to be capable of expression include the Diptera, Culicidae and Tephritids, all of which are particularly preferred. It will be appreciated that any one system of the present invention may be capable of expression in all, some, or one, of the orders exemplified above. A preferred system is expressible in all of the orders exemplified.

In a further aspect, the gene expression system described herein may be used to monitor transgenic insects. For example, it may be used to monitor transgenic insects in SIT programmes and as such, it is preferable that the gene expression system is used in pest insects, as defined above.

In a further aspect, there is provided a method of expressing a marker gene in an insect. Preferably, the method comprises transforming the insect with the present expression system. This may also be applied to be a method of transforming an insect.

Also provided is a method of insect identification, or quality control, comprising expressing the marker gene, via the present expression system, in insects. The preferred insects are described herein.

BRIEF DESCRIPTION OF THE FIGURES

The accompanying Figures serve to illustrate the present invention.

FIG. 1 shows the DNA sequence of the Mexfly Muscle actin promoter and 5'UTR region used in construct #4014;

FIG. 2 is a plasmid map of #4104, showing a map of the Mexfly muscle actin promoter (MexMuAc pro) construct containing: MexMuAc promoter driving DsRed2 fluorescent protein; known transformation marker, Hr5IE1-zs-green; piggy bac ends for transformation into insect cells; bacterial origin of replication (puC ori) and ampicillin resistance gene (bla (amp[R]) for growth and selection in *Escherichia coli*;

FIG. 3 shows the DNA sequence of the *Bombyx mori* muscle action promoter (BmA1) fragment (SEQ ID NO: 5);

FIG. 4 is a plasmid map of #4143;

FIG. 5 is a plasmid map of #4247;

FIG. 6 shows the DNA sequence of *Aedes aegypti* muscle actin promoter fragment (SEQ ID NO: 6);

FIG. 7 is a plasmid map of #4133;

FIG. 8 shows the DNA sequence of 5' UTR (including truncated intron in lower case) of #4133 (SEQ ID NO: 14);

FIG. 9 shows the DNA sequence of ZsGreen of #4133 (SEQ ID NO: 18);

FIG. 10 shows the DNA sequence of DsRed 2 of #4014 (SEQ ID NO: 19);

FIG. 11 shows the DNA sequence of Sv40 3' UTR (SEQ ID NO: 20); and

FIG. 12 shows the DNA sequence of Mexfly muscle actin 3' UTR (SEQ ID NO: 21).

DETAILED DESCRIPTION OF THE INVENTION

Systems of the present invention may be used in order to express any suitable marker protein. For the sake of convenience, such marker proteins will frequently be referred to as fluorescent proteins herein, but it will be appreciated that any such reference includes reference to all suitable marker proteins, unless otherwise apparent from the context.

Expression of a fluorescent protein is desirable for several applications including (i) identification of transgenics in the process of transformation, (ii) identifying the presence of the transgene in laboratory strains and experiments, (iii) identifying the presence of the transgene in released insects and their descendants, e.g. following trapping.

The expression should be strong so as to be readily scored, e.g. against background, or in older specimens (e.g. which have been dead for some time before scoring). The expression should ideally be in most, or all, body parts and developmental stages, so that presence can be determined in all or most life cycle stages and in incomplete or damaged specimens. Yet expression, especially strong expression, may impose undesirable fitness penalties, such as those driven by cytoplasmic actin promoters, as explained above, or weak expression. Accordingly, it is desirable to restrict expression to a single tissue. This should improve fitness unless the tissue happens to be particularly sensitive to expression.

Muscle fits the above criteria. Muscle promoters make strong candidates for such expression given that muscle tissue is ample in any organism both spatially and temporally. Furthermore, it is possible to systematically identify, by homology, highly expressed muscle-specific proteins, which are the structural proteins of muscles. We have identified such a muscle promoter and shown that it does indeed give very strong, clear expression of a fluorescent reporter in two tephritid fruit flies, and in moths, *Plutella xylostella* and pink bollworm. Moths in general, and these species in particular, are a preferred target insect in which the system is expressed.

It is preferred to distinguish between muscle actin and non-muscle, or cytoplasmic actin, which is found in essentially every cell and which, therefore, tends to have much broader expression in terms of tissue and cell types. A further benefit of tissue-specific expression, rather than constitutive expression, is that expression in different tissues can, in principle, be scored independently. Moreover, it is preferred to distinguish between muscle actin and indirect flight muscle actin (Allen M L, Christensen B M 2004). Expression of indirect flight muscle actin is substantially restricted to the indirect flight muscle. Consequently, it is expressed in fewer body regions, essentially just the thorax, and in fewer developmental stages, being late larvae, pupae and possibly through into adults, than 'conventional' muscle actins. As noted above, restricted spatial expression markers make it ineffective for field monitoring purposes, as trapped insects may lose significant part of their bodies in a trap, resulting in misidentification and recording of the caught insects in a control programme.

Accordingly, in some embodiments, the indirect flight muscle actin is excluded, especially Act88F from *Drosophila*.

There are various muscle actin promoters in some insects, so the invention preferably provides those that express across at least two, and preferably 3, or even all, life cycle stages, which is clearly an advantage for detection, for instance. Thus, any two of egg, larval, pupal or adult expression is preferred, and preferably consecutive stages. In addition to, or in combination with, any of theses, it is also preferred that that expression is across at least two and preferably all body segments of an insect, being the head, thorax and abdomen. It is particularly preferred that the expression is seen in all, or at least the abdomen and/or thorax, body sections in adults.

Surprisingly, despite widespread and strong expression of the fluorescent protein conferred by the muscle actin promoter, we have found that no fitness disadvantage was conferred on the transgenic insect. Thus, the gene expression system of the present application obviates the need for the use of dyes or powders and alleviates the disadvantages associated with these methods, including those of adverse health effects on the handlers and the possibilities of human error.

As such, it is preferred that expression of the marker gene, e.g. a fluorescent protein, under the control of the muscle actin promoter is sufficiently strong that the transgenic individuals are easily recognizable. This is particularly the case if they are recognisable by the naked eye. Ideally, this will be at all, or two or 3, of the larval, pupal and, in some cases, adult stages. It is also preferred that the expression, preferably strong expression, of the marker gene, such as fluorescent protein, confers little or no fitness disadvantage, preferably such that little or no the effects of the transgene are observed in any of the transgenic strains.

Actin is a globular multi-functional protein that forms microfilaments. It is present in all eukaryotic cells at high concentrations. In muscle fibres, actin comprises 20% of total cellular protein by weight. Actin has been one of the most highly conserved proteins throughout evolution, because it interacts with a large number of other proteins. It has 80.2% sequence conservation at the nucleotide level between *Homo sapiens* and *Saccharomyces cerevisiae*, and 95% conservation of the primary structure of the protein product. Although most yeasts have only a single actin gene, higher eukaryotes, in general, express several isoforms of actin encoded by a family of related genes. Mammals have at least six actin isoforms coded by separate genes, which are divided into three classes, alpha, beta and gamma, according to their isoelectric points. In general, alpha actins are found in muscle, whereas beta and gamma isoforms are prominent in non-muscle cells. Although the amino acid sequences and in vitro properties of the isoforms are highly similar, these isoforms cannot completely substitute for one another in vivo (Perrin and Ervasti, 2010).

Considering the high expression of muscle actin in eukaryotic organisms, indicative of strong promoter sequences, and the conserved nature of the genes involved, we decided to identify and utilise these promoters as potential transformation markers with reliable field properties; i.e. sustainable fluorescent expression in dead tissue. To this end, the muscle actin promoter from the Mexican fruit fly, *Anastrepha ludens*, was identified and isolated as described in the example below. It should be noted that there will often be more than one muscle actin gene in an insect genome. A person skilled in the art would recognise that any variant of the muscle actin promoter may be used with the gene expression system described herein.

The marker may also be considered to be a reporter.

The gene expression system may also comprise further genes (i.e. polynucleotide sequences for expression, e.g. of a transgene), the expression of the marker serving to indicate the presence of that transgene or its associated trait in an individual. This may be used as an indicator of successful transformation, or of the inheritance of the transgene in the progeny of a transformant (i.e. in an insect line).

Expression of the marker protein can be used to allow the assessment of the degree of inclusion of a transgene, or other effector, into the population. This has several advantages, including that, like any such marker, it identifies the presence of the transgene, so one can follow inheritance. The more tightly the marker is linked to the trait of interest e.g. a lethal system, the less likely it is that mutations occur which inactivate one but not the other. In practice, though, if the marker and transgene are on the same inserted DNA segment, then this is extremely unlikely in any case.

The polynucleotides making up the present expression system may be DNA, RNA or a mixture of both.

The system may be inducible or it may be repressible. Suitable examples exist in the art, including GAL4-UAs or the tet-on or tet-off systems, described for instance in our RIDL PCT publication mentioned hereinabove. Expression of the marker gene may therefore be induced or de-repressed, for instance by removal of tetracycline from the environment, such as the diet, of the insect.

In a further aspect, a method of quality control is hereby provided, comprising expressing the present expression system in a target group of individuals and determining whether those individuals meet expected criteria such as size, number, developmental stage or localisation. For instance, if the marker gene is a reporter such as a fluorescent protein, then the individuals where expression from the system occurs will become visible under suitable wavelengths of light. This method may further comprise inducing or de-repressing expression of the present expression, for instance as mentioned above, so that the individuals where expression from the system has been induced or de-repressed will become visible under suitable wavelengths of light.

Although cytoplasmic actin promoters have been used in the past as transformation markers (see above and below), this is the first use of a muscle actin promoter being used for a similar purpose. Furthermore, we have successfully utilised the same plasmid, #4014, FIG. 2, in two different Tephritids; the Mediterranean fruit fly, *C. capitata*, and the Olive fly, *B. oleae*, with similar transgenic insect phenotypes and levels of DsRed2 expression. To our surprise, expression of the DsRed2 fluorescent protein under the Mexfly muscle actin promoter is so strong that transgenic individuals are easily recognizable by the naked eye at all larval, pupal and in some cases adult stages. Moreover, despite the strong DsRed2 expression, no adverse effects of the transgene have been encountered in any of the lines we have generated so far; strains have been kept in our laboratories for more than 2 years. OX4676 was also used in both species.

We have tested Medfly adults containing either the IE1-Hr5 or polyubiquitin promoter sequences driving fluorescent proteins, in various simulated trapping conditions, under a number of different temperature and humidity environments, and found that although both markers express well in dead tissue for a week, the accuracy of identification between a transgenic and wild type insects drops considerably after longer periods on a trap. However, fluorescence was identified accurately in the same experiment, after a month in a trap, in Medfly individuals carrying the Mexfly-muscle actin promoter—DsRed2 plasmid, #4014, FIG. 2. Furthermore, in the latter case, Medflies did not require removal from the trap, which is usually required, as commonly used yellow sticky traps exhibit quite a strong colouring under various excitation filters.

Owing to the conserved nature of the actin genes, similar, or the same, muscle actin promoters may be used other insects, for example Lepidoptera, coleopterans and mosquito species, with minimal genetic manipulation. We have also isolated a muscle actin promoter from *Bombyx mori*, and have prepared a gene expression system comprising the same. This gene expression system was tested in Pink Bollworm (Example 5). The results were comparable to Medfly individuals transformed with #4014 construct. Moreover, we have also isolated a muscle actin promoter from *Aedes aegypti* based on homology to published genome sequence.

Particularly preferred is a muscle actin promoter from *Bombyx Mori* or *Aedes Aegypti*, and most preferably from Mexfly.

A muscle actin promoter from other species may also be used and, in some embodiments, the origin of the promoter will tally with the species in which it is expressed (i.e. the species to be transformed). In other embodiments, a muscle actin promoter from one species may be used for expression of the fluorescent protein in another species. That other species may be in the same class (i.e. another insect), but more preferably in the same order or family, and most preferably in the same genus as the organism to be transformed.

As such, a muscle actin promoter may be isolated from any insect, preferably from the order Diptera or the order Lepidoptera.

More preferably, the muscle actin promoter may be from a Culicidae and, most preferably, from a mosquito, preferably from the genera *Stegomyia, Aedes, Anopheles* or *Culex*. Particularly preferred are *Stegomyia aegyptae*, also known as *Aedes aegypti, Stegomyia albopicta* (also known as *Aedes albopictus*), *Anopheles stephensi, Anopheles albimanus* and *Anopheles gambiae*.

It is also preferable that the muscle actin promoter is from a Tephritid, preferably from Medfly (*Ceratitis capitata*), preferably from Mexfly (*Anastrepha ludens*), preferably from Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*). Medfly (*Ceratitis capitata*), Mexfly (*Anastrepha ludens*), or Olive fruit fly (*Bactrocera oleae*) are particularly preferred.

Within Lepidoptera, moths are particularly preferred, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae.

The muscle actin promoter is also preferably from *Drosphila melanogaster*. Most preferably, it is that provided in SEQ ID NOS: 5 or 6 and most preferably SEQ ID NO: 1 or variants of any thereof.

Gene expression systems of the present invention, comprising a muscle actin promoter from the any of the above organisms, may be expressed in a range of insects.

It is preferred that the gene expression system is capable of expression in Dipterans and most preferably Tephritids, Medfly (*Ceratitis capitata*), Mexfly (*Anastrepha ludens*), preferably Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*).

Where a list of options is provided herein, such as the list of insect types in which it is preferred that the systems of the present invention can be expressed, it will be appreciated that the present invention contemplates each member of that list individually, as well as being part of that group.

It is also particularly preferred that the gene expression system is capable of expression in a mosquito, preferably from the genera *Stegomyia, Aedes, Anopheles* or *Culex*. Particularly preferred are *Stegomyia aegyptae*, also known as *Aedes aegypti, Stegomyia albopicta* (also known as *Aedes albopictus*), *Anopheles stephensi, Anopheles albimanus* and *Anopheles gambiae*.

Expression in Lepidoptera is also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae.

In a further aspect, expression may be in a beneficial insect. A beneficial insect, in the context of the present invention, is, for example, a pollinator and/or is a predator or parasitoid, parasite suitable for controlling agricultural or horticultural pests. Especially preferred are bees, including honeybees, bumblebees and other pollinators. Some bees are pollinators, whilst others are predators or act as parasites. Thus, predatory or parasitic bees and wasps may also be preferred beneficials. Another preferred group of beneficials are ladybugs. The preferred beneficial can also be selected from the group consisting of: Minute Pirate Bugs; Big Eyed Bugs; Assassin Bugs; Damsel Bugs; Mealybug Destroyer; Soldier Beetle; Green Lacewing; predatory mites, e.g. *Amblyseius swirskii, Phytoseulius persimilis, Typhlodromus*

*pyri* and *Amblyseius fallacis*, Syrphid Fly; Tachinid Fly; Ichneumon wasps, e.g. *Aphidius* spp., Aphelinid Wasps, e.g. *Encarsia* spp. and Trichogramma wasps.

It is particularly preferred that the gene expression system comprises a muscle actin promoter from *Bombyx mori* or *Aedes aegypti*, and most preferably from Mexfly, and can be expressed in any of the above insects.

However, it will also be appreciated that any combination of the various promoters discussed herein can be used in any of the insects discussed herein. One particularly preferred example is the use of a muscle actin promoter from *Bombyx mori* or *Aedes aegypti*, and most preferably from Mexfly in Tephritids, especially fruit flies. Another particularly preferred example is the use of a muscle actin promoter from *Bombyx mori* or *Aedes aegypti*, and most preferably from Mexfly in mosquitoes, especially *Aedes*, including *Aedes aegypti*. Another particularly preferred example is the use of a muscle actin promoter from *Bombyx mori* or *Aedes aegypti*, and most preferably from Mexfly in moths, especially *Bombyx mori* or *Plutella xylostella*.

Another particularly preferred example is the use of a muscle actin promoter from *Bombyx mori* or *Aedes aegypti*, and most preferably from Mexfly in Medfly (*Ceratitis capitata*). Another particularly preferred example is the use of a muscle actin promoter from *Bombyx mori* or *Aedes aegypti*, and most preferably from Mexfly in Olive fly (*Bactrocera oleae*). Another particularly preferred example is the use of a muscle actin promoter from *Bombyx mori* or *Aedes aegypti*, and most preferably from Mexfly in Pink Bollworm.

The insect in which the present system is expressed may be referred to as a transformant, or may be considered to be the progeny thereof, or as a host. The insect may be a pest, for instance a disease vector, for instance a mosquito species that may carry the malarial parasite or act as a vector for dengue fever, or an agricultural pest, for instance moths or flies, especially fruit flies.

The system described herein is suitable for expression in an insect, but it will be understood that this may also be preferably referred to as "capable of expression in" or "adapted to or having the ability to express in an insect". It is preferable that insects are transformed with the gene expression system by injection into embryos.

Plasmids, or other suitable vectors, may be used as vehicles for the expression systems of the present invention, and may be introduced into the population by any suitable transformation means known in the art.

A promoter is typically understood to be a region of DNA sufficient to initiate transcription of a gene, and should preferably include features such as promoter elements such as transcription factor and RNA polymerase binding sites. It may comprise further regulatory elements such as enhancers, and extended regions of DNA for 5' and 3' UTRs which enhance expression of the gene. The skilled person would be able to assess which features are necessary for improved expression of the gene. A particularly preferred 3' UTR is the 3' UTR of the muscle actin gene from *Anastrepha ludens*.

When a muscle actin promoter is referred to as being "isolated from", "taken from" or simply "from" a particular species, it will be understood that it does not necessarily mean that the particular DNA is derived from an organism belonging to that species. Instead, it will be understood that it means that the DNA sequence is largely, or completely, identical to that found in the genome of the wildtype of that species. The extraction or isolation may have occurred in the past and may have been used in the transformation of the host insect's ancestors.

The gene expression system comprises a muscle actin promoter "operably linked" to a marker gene. In this context, it will be understood that this means that the promoter is suitable or capable of driving transcription of the marker gene. It is generally preferred that they are situated substantially adjacent each other and not separated by more than 3 or 4 kbp.

By "gene" herein is meant principally a sequence encoding an effector. In this case, the effector is largely a protein so as to function as a marker, as required, generally so as to express a detectable marker. Preferably, the marker is a protein, which confers a detectable change in phenotype of the insect.

A marker gene is a gene used to determine if a nucleic acid sequence has successfully transformed an organism such that it is being expressed. The nucleic acid sequence may, for example, encode a functional protein which causes sterility in an insect. The marker gene may be considered as a screening marker as opposed to a selectable marker, which may protect the organism from a selective agent that would normally kill it or prevent its growth, such antibiotic. A marker for screening will cause the cells containing the marker gene to appear different to those that, for instance, have not been transformed or which do not contain the transgene. A preferred example of a screening marker is a fluorescent protein, such as GFP.

As such, it is preferable that the marker gene of the expression system described herein encodes a fluorescent protein. It is particularly preferred that the fluorescent protein is a green fluorescent protein (GFP), ZsGreen, TurboGFP, yellow fluorescent protein (YFP), mCitrine, DsRed, DsRed2, mCherry, AmCyan, CyPet and other members of the GFP-like protein super-family. These proteins are typically derived from marine invertebrates, e.g. anemones, and when expressed emit fluorescence after exposure to bright light of a specific excitation wavelength. Fluorescent proteins are widely used for transgenic research purposes.[3]

In the red spectrum any of the following are preferred: DsRed-Express, tdTomato, DsRed monomer, AsRed2, mstrawberry, mcherry, mRaspberry, E2-Crimson, or mPlum.

In the green spectrum, either of the following is preferred: EGFP, AcGFP1.

The marker gene may encode other proteins manifesting a phenotype which varies depending on the level of expression. This has the advantage of allowing qualitative or quantitative analysis for screening.

Where reference to a particular nucleotide sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

We therefore report a unique marker system and methods for simple and reliable monitoring of released insects in the field that confers significant cost benefits to a SIT control pest programme and requires minimal training of personnel. Released males may also be identified by farmers and workers in the field with the use of a portable lamp with the appropriate excitation wavelengths, eliminating the need for the traps to be transferred to a laboratory facility for careful examination and identification of the trapped insects. Also, the use of such a marker allows for the development of a highly accurate, automated detection and monitoring system based on computer software, which is able to detect the phenotype conferred by the marker gene of the expression system.

EXAMPLES

Example 1

Mexfly Muscle Actin

Mounier et al (1992) compared the sequences of insect muscle and cytoplasmic actins and identified Bm A1 (from *Bombyx mori*), Dm Act57A and Dm Act87E (both from *Drosophila melanogaster*) as muscle actins. The cDNA sequences of these 3 genes were aligned using CLUSTALW, and the following degenerate primers designed:

```
364) BmA1degF
                                    (SEQ ID NO: 2)
GATGTGYGACGAYGATGTTMG 365) BmA1degR
                                    (SEQ ID NO: 3)
CTTCTCSAGGGANGTGGAGGCG
``` which amplify a 718 bp product. These primers were used for PCR on Mexfly adult female cDNA using Phusion polymerase. The resulting PCR product was cloned and sequenced. The sequence (confirmed by BLAST comparison to GenBank sequences) was extended by 5' and 3' RACE in order to obtain the complete mRNA sequence.

The promoter sequences was isolated from the coding sequence of the Mexfly Muscle actin gene using

```
453) Mexmuf1R
                                    (SEQ ID NO: 4)
CATTRTCAACRACCARAGCAGCA 454) MexmuF1Rn
                                    (SEQ ID NO: 7)
CAGCAACATCRTCGTCGCACATC
``` in adaptor-mediated PCR as follows:

Mexfly genomic DNA was digested with ClaI, BamHI and SphI restriction enzymes. It was ligated to adaptors consisting of an appropriate sticky end for ligation to the digested DNA and primer annealing sites for primers:

```
222) PRIMER:
                                    (SEQ ID NO: 8)
GTGTAGCGTGAAGACGACAGAA

223) MID
                                    (SEQ ID NO: 9)
GACGACAGAAAGGGCGTGGTG.
```

PCR was carried out on these templates using 222) Primer and 453) MexmuFIR. The resulting PCR product was diluted 1 in 100 then used as a template for nested PCR using primers 223) MID and 454) MexmuFIRn. These PCR products were cloned using the TOPO PCR cloning kit (invitrogen) and sequenced.

Primers

```
464) MexmuAcRn2
                                    (SEQ ID NO: 10)
TCACACCGCGCTCATCGTCA 465) MexmuAcRn3
                                    (SEQ ID NO: 11)
CACGTTAATGTTGAGCTGCATGG 466) MexmuAcRn4
                                    (SEQ ID NO: 12)
ATCCGAGCGAGTCAGCAACAAC
``` were designed from this sequence to use on the same ligated DNA templates using Primer and mid primers as before. This extended the promoter sequence further.

A 2.2 kb sequence incorporating the promoter and 5'UTR (untranslated region) (FIG. 1) were cloned in front of the start ATG codon of DsRed2 fluorescent protein (FIG. 10), in a plasmid (#4104, FIG. 2) also containing piggy bac transposon ends and the transformation marker, Hr5IE1-zsgreen. #4104 contains MexMuAc promoter driving DsRed2 fluorescent protein; known transformation marker, Hr5IE1-zsgreen; piggybac ends for transformation into insect cells; Sv40 3' UTR sequence (FIG. 11), bacterial origin of replication (puC ori) and ampicillin resistance gene (bla (amp [R])) for growth and selection in *Escherichia coli*.

Regarding FIG. 2, OX4676 was used in both species. Others were used for both olive fly and medfly with the single difference that we used 4-ended piggybac constructs for medfly and single ended piggybac constructs for olive fly. Despite the different numbers, all constructs utilised the exact same sequences relating to the transformation marker.

This is the first demonstration of DsRed2 expression under the Mexfly muscle actin promoter. The plasmid utilises a green fluorescent protein (ZsGreen; clontech) under a generic promoter-enhancer sequence; Hr5-IE1 as a transformation marker. As we did not know at that stage whether the isolated DNA sequence upstream of the Mexfly muscle actin gene served as an adequate promoter sequence to drive DsRed2 expression, even more so in another Tephritid; *Ceratitis capitata*, we thought it best to utilise a promoter sequence known to function well previously to drive the expression of a different fluorescent protein; ZsGreen in order to identify transformed individuals. Both markers utilised the bi-directional SV40 3' UTR previously functional in a number of different insect species.

530 pre-blastoderm Medfly embryos were injected with a piggybac transposon-transposase mix (600:300 ng/μl, respectively). 260 GO adults were back-crossed to wild type of the opposite sex, in pools of 10. Progeny was collected and screened for the presence of both fluorescent proteins. 8 independent insertion events were generated. All lines exhibited green fluorescence under the appropriate excitation wavelength as expected. Furthermore, all lines displayed a strong red expression in all muscle tissue under the appropriate wavelength. Fluorescence was clearly detectable in all developmental stages. No recordable differences were observed among siblings of the same strain, indicating a uniform and ubiquitous expression. Red expression was so strong in most of the strains analysed that a pink hue was clearly visible at mid-late larval and early-mid pupal stages with naked eye; that is transformed individuals were evident with 100% accuracy without the need of a standard microscope equipped with the appropriate excitation filters for the fluorescent protein used (DsRed2 in this particular case), a standard procedure for fluorescent screening. Adult colouration was not apparent in any of these strains. Nevertheless, all adults—at all ages—displayed a strong red expression when examined under a suitable microscope. Two of these strains were tested in parallel with other Medfly strains utilising Hr5-IE1 and polyubiquitin promoter sequences driving expression of DsRed2, for dead tissue fluorescence sustainability under various trapping methods and simulated environmental conditions and clearly outperformed existing markers.

4014 Medfly strains have been continuously reared in our premises for over 40 generations without an observable fitness penalty in adult longevity, female egg fecundity, embryo hatching or pupal recovery.

Subsequent sperm-lethal constructs (#4676, #4705 #4751 and #4718) (GB2500113 and WO2013/131920) used the Mexfly muscle actin 3'UTR (FIG. 12), which resulted in stronger expression. Therefore, one way of making the Bombyx muscle actin promoter stronger, may be to incorporate its 3'UTR into the construct.

Example 2

4751 (PB-MexMActPro-DsR-tetO21-Prota-SG4-mCh-SG4-FokI-CcBTubPro-tTAV2-Cci-tTAV3)

Given the desirable properties of the Mexfly muscle actin promoter as a transformation marker and monitoring tool, we decided to further utilise this promoter in conjunction with our newly developed sperm lethal technology (GB2500113) In this instance and in all examples following, we have utilised the 3' UTR of the muscle actin gene from *Anastrepha ludens*. Plasmid #4751 was injected in preblastoderm Medfly embryos as described above. Two different transformation events were attained. Both strains displayed robust red fluorescence under a suitable microscope and a "light red" phenotype clearly visible with naked eye at larval and pupal stages. In one of the two strains, visible colouration was apparent even at the adult stage, irrespective of the dark exoskeleton processed by this species. This may indicate an improved expression of the fluorescent protein possibly through utilisation of its own UTR sequence. As before, no detrimental effects were observed in either strain for any rearing parameter.

Example 3

OX4676 (PB-Mex-mActin-DsRed-tra-ubi-ZsGreen1)

In most cases, an insect male has the capacity of mating more than one female whilst females of most species usually mate only once in their lifetime. This means that one could exploit double, triple or even multiple the amount of females, compared to the amount of males, in mass-rearing cages to increase egg yield and therefore production of males for release in a cost-effective manner. This is in operation in Medfly mass-rearing factories today, utilising the white pupae mutation associated with the TSL (temperature sensitive lethal) sexing strains; females are white as pupae compared to males that display the "normal" brown pupal phenotype. Nevertheless, the white pupae mutation or any other phenotypic mutation that can be used in a similar way has to be isolated, characterised and cloned separately for all insect pests that SIT can be applied to, a laborious and costly procedure.

Development of differential fluorescent expression in males and females is a far less strenuous, affordable and thus widely applicable way of achieving similar outcomes in a number of different insect species of interest, with none or minimal manipulation among species. To investigate this possibility, we have developed construct #4676 where the Mexfly muscle actin promoter drives expression of DsRed2 in males and females but also drives expression of ZsGreen in females only. For female specificity, we have utilised the same sex specific alternative splicing described and patented prior to this experiment (PCT/GB2007/000488). Insertion of a cassette exon from the *C. capitata* transformer gene between the DsRed2 and ZsGreen DNA sequences means that the ZsGreen transcript is disrupted in male splice variants but not in the female-specific ones.

This construct has been injected in Medfly and Olive fly pre-blastoderm embryos. 4 independent insertion events were generated in Medfly and 7 in olive fly. Males and females of all strains—both species—exhibited the red fluorescent phenotype, while females only of all strains displayed the green fluorescent phenotype under the appropriate excitation filters. In other words, transposition of this construct to two different Tephritids resulted in the expected phenotype. Nevertheless, none of the strains displayed the strong fluorescent expression seen previously with this promoter. This could be the result of a very long and thus unstable transcript being produced which may comprise expression levels. Furthermore, green fluorescence was sometimes hard to detect in females of some strains—especially in Medfly, possibly due to positional effects.

Example 4

4705 (PB MexMActPro-DsR-tetO21-Prota-mCh-FokI-CcBTubPro-tTAV2)

This is a single piggybac construct utilising our novel "sperm lethal" technology discussed in Example 2 in combination with our unique transformation marker promoter from *A. ludens*. The transposon was co-injected with piggybac transposase mRNA (600: 500 ng/μl) into preblastoderm olive fly embryos. Ten independent transgenic strains were generated all displaying a very strong and ubiquitous fluorescent phenotype under a suitable microscope and different hues of red colouring in larvae and pupae.

Example 5

*Bombyx mori* Muscle Actin

BmA1 promoter was identified by BLAST of the published coding sequence against the published *Bombyx mori* genomic sequence (whole genome sequencing project: http://silkbase.ab.a.u-tokyo.ac.jp/cgi-bin/index.cgi). A 2.58 kb fragment 5' of the gene was amplified as the promoter fragment, from *Bombyx mori* genomic DNA (FIG. 3).

Using plasmid DNA amplified and purified by Midiprep or MaxiPrep, DNA mixes were prepared to a final concentration of 500 ng/μl and 300 ng/μl of construct and helper plasmid (making piggybac transposase), respectively, after final re-suspension in injection buffer. 1467 embryos were injected with this construct (#4143, FIG. 4), resulting in 238 survivors and 1 line. The green fluorescence was observed in transgenic insects.

Construct #4143 (FIG. 4) consists of *Bombyx mori* BMA1 muscle actin promoter driving zsgreen fluorescent protein; known transformation marker Baculovirus OPIE2 promoter driving DsREd2; PB transposon ends for transformation into insects; bacterial origin of replication (pUC on) and ampicillin resistance gene (bla AmpR) for growth and selection in *E. coli*.

Construct #4247 was also injected (FIG. 5). The only difference between this and #4143 (FIG. 4) is that there are an extra 340 nucleotides at the beginning of the promoter (5' end) and it also includes 66 bp comprising the 5'UTR at the 3' end of the promoter (which should make the promoter much more efficient). 1945 embryos were injected with this construct resulting in 588 survivors.

Example 6

*Aedes aegypti* Muscle Actin

Similarly, the published genome sequence from *Aedes aegypti* (http://aaegypti.vectorbase.org/) was searched using BLAST for homology to the Mexfly Muscle actin gene. This identified *Aedes* Actin1 as the muscle actin gene. This gene has a large intron in the 5'UTR (FIG. 8), which was truncated in the construct (#4133, FIG. 7). The promoter (FIG. 6) was amplified in two fragments using the following primer pairs:

```
723) AemuAcproAscF
                                       (SEQ ID NO:_13)
GGCGCGCCGTTCGAGCAGTAGACCCACCAACC 724) AemuAcintSphR
                                       (SEQ ID NO:_14)
GCATGCTATGCCTTAGGAAGCCCTGCCG 725) AemuAcintSphF
                                       (SEQ ID NO:_15)
GCATGCCGTATATCGAGTGGCAAGCTCGAAG 726) AemuAcproNheR
                                       (SEQ ID NO:_16)
GCTAGCCAACCGTCTATTCGCATAGTACAATTCC.
```

SEQUENCES

SEQ ID NO: 1—MexFly muscle actin promoter and 5' UTR region used in construct #4014
SEQ ID NO: 2—BmA1degF Primer
SEQ ID NO: 3—BmA1degR Primer
SEQ ID NO: 4—453) MexmufIR
SEQ ID NO: 5—*Bombyx mori* muscle actin promoter
SEQ ID NO: 6—*Aedes aegypti* muscle actin promoter
SEQ ID NO: 7—454) MexmuFIRn
SEQ ID NO: 8—222) PRIMER
SEQ ID NO: 9—223) MID
SEQ ID NO: 10—464) MexmuAcRn2
SEQ ID NO: 11—465) MexmuAcRn3
SEQ ID NO: 12—466) MexmuAcRn4
SEQ ID NO: 13—723) AemuAcproAscF
SEQ ID NO: 14—724) AemuAcintSphR
SEQ ID NO: 15—725) AemuAcintSphF
SEQ ID NO: 16—726) AemuAcproNheR
SEQ ID NO: 17—5'UTR (including truncated intron in lower case) of #4133
SEQ ID NO: 18— DNA sequence for ZsGreen of #4133
SEQ ID NO: 19—DNA sequence for DsRed2 of #4014
SEQ ID NO: 20— Sv40 3' UTR Sequence
SEQ ID NO: 21—Mexfly muscle actin 3' UTR sequence

REFERENCES

Allen, M., Handler, A., Berkebile, D., and Skoda, S. (2004). "piggyBac transformation of the New World screwworm, *Cochliomyia hominivorax*, produces multiple distinct mutant strains." Med. Vet. Entomol., 18, pp. 1-9.

Allen, M., O'Brochta, D., Atkinson, P., and Levesque, C. (2001). "Stable, germ-line transformation of *Culex quinquefasciatus* (Diptera: Culicidae)." J. Med. Entomol., 38(5), pp. 701-710.

Allen, M., Christensen, B., (2004) "Flight muscle-specific expression of act88F: GFP in transgenic *Culex quinquefasciatus* Say (Diptera: Culicidae)." Parasitology International, 53, pp. 307-314.

Alphey, L., Nimmo, D., O'Connell, S., and Alphey, N. (2008). "Insect population suppression using engineered insects", in S. Aksoy, (ed.), Transgenesis and the management of vector-borne disease. Austin, Tex., Landes Bioscience, pp. 93-103.

Bakri, A., Mehta, K., and Lance, D. R. (2005). "Sterilizing insects with ionizing radiation", in V. A. Dyck, J. Hendrichs, and A. S. Robinson, (eds.), Sterile Insect Technique. Principles and practice in area-wide integrated pest management. The Netherlands, Springer, pp. 233-268.

Berghammer, A. J., Klingler, M., and Wimmer, E. A. (1999). "A universal marker for transgenic insects." Nature, 402(6760), pp. 370-1.

Burn, T., Vigoreaux, J., and Tobin, S. (1989). "Alternative 5C actin transcripts are localized in different patterns during *Drosophila* embryogenesis." Developmental Biology, 131 (2), pp. 345-355.

Catteruccia, F., Benton, J., and Crisanti, A. (2005). "An *Anopheles* transgenic sexing strain for vector control." Nature Biotechnology, 23(11), pp. 1414-1417.

Catteruccia, F., Godfray, H. C., and Crisanti, A. (2003). "Impact of genetic manipulation on the fitness of *Anopheles stephensi* mosquitoes." Science, 299(5610), pp. 1225-7.

Catteruccia, F., Nolan, T., Loukeris, T., Blass, C., Savakis, C., Kafatos, F., and Crisanti, A. (2000). "Stable germline transformation of the malaria mosquito *Anopheles stephensi*." Nature, 405(6789), pp. 959-962.

Chalfie, M., Tu, Y., Euskirchen, G., Ward, W. W., and Prasher, D. C. (1994). "Green fluorescent protein as a marker for gene expression." Science, 263(5148), pp. 802-805.

Dyck, V. A., Hendrichs, J., and Robinson, A. S. (2005). "Sterile Insect Technique: Principles and practice in Area-Wide Integrated Pest Management". City: Springer: The Netherlands, pp. 801.

Franz, G. (2002). "Recombination between homologous autosomes in medfly (*Ceratitis capitata*) males: type-1 recombination and the implications for the stability of genetic sexing strains." Genetica, 116, pp. 73-84.

Fraser, M. J., Jr. (2012). "Insect Transgenesis: Current Applications and Future Prospects." Annual Review of Entomology, 57(1), pp. 267-289.

Graham, H. M., and Mangum, G. L. (1971). "Larval diets containing dyes for tagging pink bollworm." J Econ Entomol, 64, pp. 377-379.

Hagler, J., and Jackson, C. (2001). "Methods for marking insects: current techniques and future prospects." Annu. Rev. Entomol., 46, pp. 511-543.

Hagler, J. R., and Miller, E. (2002). "An alternative to conventional insect marking procedures: detection of a protein mark on pink bollworm by ELISA." Entomol Exp Appl, 103(1), pp. 1-9.

Handler, A., and Harrell, R. (2001). "Polyubiquitin-regulated DsRed marker for transgenic insects." BioTechniques, 31, pp. 820-8.

Handler, A., and Harrell, R. A. I. (1999). "Germline transformation of *Drosophila melanogaster* with the piggyBac transposon vector." Insect Mol Biol, 8, pp. 449-457.

Horn, C., Schmid, B., Pogoda, F., and Wimmer, E. (2002). "Fluorescent transformation markers for insect transgenesis." Insect Biochem Mol Biol, 32(10), pp. 1221-35.

Irvin, N., Hoddle, M. S., O'Brochta, D. A., Carey, B., and Atkinson, P. W. (2004). "Assessing fitness costs for transgenic *Aedes aegypti* expressing the GFP marker and transposase genes." Proc Natl Acad Sci USA, 101(3), pp. 891-6.

Knipling, E. (1955). "Possibilities of insect control or eradication through the use of sexually sterile males." J Econ Entomol, 48, pp. 459-469.

Koukidou, M., Klinakis, A., Reboulakis, C., Zagoraiou, L., Tavernarakis, N., Livadaras, I., Economopoulos, A., and Savakis, C. (2006). "Germ line transformation of the olive fly Bactrocera oleae using a versatile transgenesis marker." Insect Molecular Biology, 15(1), pp. 95-103.

Loukeris, T. G., Livadaras, I., Arca, B., Zabalou, S., and Savakis, C. (1995). "Gene transfer into the medfly, Ceratitis capitata, with a Drosophila hydei transposable element." Science, 270(5244), pp. 2002-5.

Marrelli, M. T., Moreira, C. K., Kelly, D., Alphey, L., and Jacobs-Lorena, M. (2006). "Mosquito transgenesis: what is the fitness cost?" TRENDS Parasit, 22(5), pp. 197-202.

Matz, M., Fradkov, A., Labas, Y., Savitsky, A., Zaraisky, A., Markelov, M., and Lukyanov, S. (1999). "Fluorescent proteins from nonbioluminescent Anthozoa species." Nat Biotechnol, 17(10), pp. 969-73.

Morrison, N. I., Franz, G., Koukidou, M., Miller, T. A., Saccone, G., Alphey, L. S., Beech, C. J., Nagaraju, J., Simmons, G. S., and Polito, L. C. (2011). "Genetic improvements to the sterile insect technique for agricultural pests." Asia Pacific J Mol Biol and Biotechnol, 18(2), pp. 275-295.

Mounier, N., Gouy, M., Mouchiroud, D., and Prudhomme, J. C. (1992). "Insect muscle actins differ distinctly from invertebrate and vertebrate cytoplasmic actins." J Mol Evol, 34(5), pp. 406-415.

Papathanos, P., Bossin, H., Benedict, M., Catteruccia, F., Malcolm, C., Alphey, L., and Crisanti, A. (2009). "Sex separation strategies: past experience and new approaches." Malaria Journal, 8(Suppl 2), pp. S5.

Parker, A. (2005). "Mass-rearing for sterile insect release", in V. A. Dyck, J. Hendrichs, and A. S. Robinson, (eds.), Sterile Insect Technique. Principles and practice in area-wide integrated pest management. The Netherlands, Springer, pp. 209-232.

Peloquin, J. J., Thibault, S. T., Staten, R., and Miller, T. A. (2000). "Germ-line transformation of pink bollworm (Lepidoptera: Gelechiidae) mediated by the piggyBac transposable element." Insect Mol Biol, 9(3), pp. 323-33.

Perera, O., Harrell, R., and Handler, A. (2002). "Germline transformation of the South American malaria vector, Anopheles albimanus, with a piggyBac-EGFP tranposon vector is routine and highly efficient." Insect Molecular Biology, 11(4), pp. 291-7.

Perrin, B. J., and Ervasti, J. M. (2010). "The actin gene family: Function follows isoform." Cytoskeleton, 67(10), pp. 630-634.

Pinkerton, A., Michel, K., O'Brochta, D., and Atkinson, P. (2000). "Green fluorescent protein as a genetic marker in transgenic Aedes aegypti." Insect Molecular Biology, 9(1), pp. 1-10.

Prasher, D. C., Eckenrode, V. K., Ward, W. W., Prendergast, F. G., and Cormier, M. J. (1992). "Primary structure of the Aequorea victoria green-fluorescent protein." Gene, 111(2), pp. 229-233.

Robinson, A. (2002). "Mutations and their use in insect control." Mutation Research, 511, pp. 113-32.

Robinson, A., and van Heemert, C. (1982). "Ceratitis capitata—a suitable case for genetic sexing." Genetica, 58(3), pp. 229-237.

Robinson, A. S., and Hendrichs, J. (2005). "Prospects for the future development and application of the sterile insect technique", in V. A. Dyck, J. Hendrichs, and A. S. Robinson, (eds.), Sterile Insect Technique. Principles and practice in area-wide integrated pest management. The Netherlands, Springer, pp. 727-760.

Rössler, Y. (1979). "The genetics of the Mediterranean fruit fly: a 'white pupae' mutant." Annals of the Entomological Society of America, 72, pp. 583-585.

Rubin, G. M., and Spradling, A. C. (1982). "Genetic transformation of Drosophila with transposable element vectors." Science, 218(4570), pp. 348-53.

Steiner, L. "Methods of estimating the size of populations of sterile pest tephritidae in release programs." Presented at Panel proceedings: Insect ecology and the sterile-male techique, Vienna.

Tamura, T., Thibert, C., Royer, C., Kanda, T., Eappen, A., Kamba, M., Komoto, N., Thomas, J.-L., Mauchamp, B., Chavancy, G., Shirk, P., Fraser, M., Prudhomme, J.-C., and Couble, P. (2000). "Germline transformation of the silkworm Bombyx mori . using a piggyBac transposon-derived vector." Nat. Biotech., 18, pp. 81-84.

The invention claimed is:

1. A polynucleotide expression system, comprising:
   a polynucleotide sequence encoding a fluorescent marker; and
   an insect muscle actin promoter comprising a nucleic acid sequence that is at least 95% identical as the nucleic acid sequence set forth in SEQ ID NO: 1, 5, or 6, operably linked to the polynucleotide sequence.

2. The polynucleotide expression system of claim 1, wherein the fluorescent marker is selected from the group consisting of green fluorescent protein (GFP), EGFP, ZsGreen, TurboGFP, AcGFPI, yellow fluorescent protein (YFP), mCitrine, DsRed, DsRed2, DsRed-Express, DsRed monomer, mCherry, mStrawberry, mRaspberry, mPlum, AmCyan, CyPet, tdTomato, AsRed2, and/or E2-Crimson.

3. The polynucleotide expression system of claim 1, further comprising an enhancer operably linked to the promoter.

4. The polynucleotide expression system of claim 1, further comprising a 5' untranslated region (UTR) and/or a 3' UTR for the polynucleotide sequence.

5. The polynucleotide expression system of claim 4, wherein the 3' UTR is from an insect muscle actin gene.

6. The polynucleotide expression system of claim 5, wherein the 3' UTR is from the insect muscle actin gene of Mexfly.

7. The polynucleotide expression system of claim 1, further comprising a transgene, wherein expression of the fluorescent marker in an insect indicates the presence of the transgene or a trait associated with the transgene in the insect.

8. The polynucleotide expression system of claim 1, wherein expression of the fluorescent marker in an insect is inducible, repressible, and/or derepressible.

9. An insect comprising, in its genome, the polynucleotide expression system of claim 1.

10. A method, comprising:
    transforming an insect with the polynucleotide expression system of claim 1.

11. The method of claim 10, further comprising detecting fluorescence due to expression of the fluorescent marker in at least two developmental stages selected from the group consisting of the egg, larval, pupal, and adult developmental stages of the insect.

12. The method of claim 11, wherein the fluorescence is visible to the naked eye at the larval, pupal, and adult stages of the insect.

13. The method of claim 10, further comprising detecting fluorescence due to expression of the fluorescent marker in at least two body segments of the insect.

14. The method of claim 13, wherein the body segments are selected from the group consisting of the head, thorax, and abdomen.

15. The method of claim 10, wherein the polynucleotide expression system confers no detectable fitness disadvantage on an insect when the fluorescent marker is expressed in the insect.

16. The method of claim 10, further comprising detecting fluorescence with the naked eye.

17. The method of claim 10, wherein the insect is of the order Diptera or Lepidoptera.

18. The method of claim 10, wherein the insect is of the family Culicidae, Tephritidae, or Bombycidae.

19. The method of claim 10, wherein the insect is selected from the group consisting of: *Aedes aegypti, Aedes albopictus, Anopheles stephensi, Anopheles albimanus, Anopheles gambiae*, Medfly, Mexfly, Oriental fruit fly, Olive fruit fly, Melon fly, Natal fruit fly, Cherry fruit fly, Queensland fruit fly, Peach fruit fly, Caribbean fruit fly, West Indian fruit fly, codling moth, silk worm, pink bollworm, diamondback moth, Gypsy moth, Navel Orange Worm, Peach Twig Borer, rice stem borer, a moth of the family Noctuidae, and a moth of the subfamily Heliothinae.

* * * * *

SEQUENCE LISTING

```
<160> NUMBER OF SEQ ID NOS: 21

<210> SEQ ID NO 1
<211> LENGTH: 2244
<212> TYPE: DNA
<213> ORGANISM: Anastrepha ludens

<400> SEQUENCE: 1
gacccttgtg cccctgcat attttgattt attttaagct gaactagttc tacattttca      60
aacttagcgc agctcataca tgtacatatc tatatatgta agtatgtatg tatatacgtt     120
cgtgtgcatg tgcagtgtgc atgcactgtg cgcaataaaa cctgctggaa ctcatttaca    180
aagcaaaaaa ttattctttc ccatcgatta cagcattaaa atcagcgtaa gtatgtaaac     240
acgccccatt taagaatcca aaaatacttg cactccattt ccatagtgca gccaaatgca    300
tggctatttg tgtgtattta atgtatgcat atatgttcgt atatttgtat gtatgaattt    360
atgactttat attcaactcc actaaaaatt gcttttcacc attcggtggg tattcacaca    420
ttttttacat atatttcata tatcaacgct ccagaaatgc cgcttgtttt actccaaaag    480
```

```
gatgcggtgt gccggaaatt aagaaatcct gctgtccagc caatttatgt atgccactgg    540
aacggcaata acgcgtggcc atgtaaacaa atgtgggatc aacaagcaaa acgctggcca    600
agcaaagaaa ttggttagag aacaaaaata aaaagaaaca agcaattcga aagctatcat    660
ctcaacaaca attacagcaa caatacgagc aaagcgcgca gatcaaagtg gcagcacctc    720
gaaaaatcca cagaggtggc aacatggaga tgaccaaaaa tagaaatgtt taacacacag    780
aaaaaggcgc caacaacaaa acaacgtcat aaagtattca acgaaggtgc tgagcgcctc    840
tacatgcacg tacatacaca caaaaacata aaaattccta cattatgata catacataca    900
tacataggtg cttacaagtg tacctacata tttattagta tccaatacat acaaatgcaa    960
atttagatac cagtgcgtgg gggccgccac agctgagcga gagcaatacg caatgtgaga   1020
gcaccagcaa ccgaaaatat atatttaata acatatttg aaaaattaaa tgttcgaaaa   1080
tagaatattc aaaatatatt ttgtttgaaa agcgacaaaa tgatcaccgt ccggatctat   1140
tgaagcgcct gacaatgcgt gcaaaaggga tagcgattgc gtcagtatgc gcggcaataa   1200
acctcaaaca cttcatatct ctccctccac acacaacccg aaaagatcgc gcgaagcaag   1260
acgaggaatt caacaaacaa tagcaacaac acatctgcaa tgcttgtata ttgaatataa   1320
atttgttaaa gaaatttcgt gcgcacccca ccacagcatc cccattatgg tgagcgctta   1380
atagcagccg acataacgtt gacgcggcag ccttgcctta tacggcgctt ttggagcgct   1440
tttagtgggg agccgtacca attgccatgg aatatatata tttgtatgta tgtatgtatg   1500
tatgcacaaa caaacccgat gatgccgaac taaacgcgag caatctgtga gatcagcgaa   1560
cagcgagcag cgaataacga gcgaaccacc caacaaagtg attatgatca ttgctgtgac   1620
gctatgacgc cacggctcgc ttcgttcgtg ggctgagtgg ggtgcttcag tgcgcaggag   1680
cacgatcgtt gttgctgact cgctcggatg cgcgcacatc gttttccatg cagctcaaca   1740
ttaacgtgtg ggtgtgtatg cgtatatacg gcatatgacg atgagcgcgg tgtgatgggt   1800
ctatttttag tggcgttgaa aaatcgtaaa cacaacgaat ccctctttga tgtgaacgta   1860
ttggtgttgc cgctattatc tgtcattgta tcagtggatc ggtgtatcgg tgttttcgtg   1920
ttggcggtgg aggtgagaca tttgttggag cgttgcgggt gtgtggggac gtgaagcgac   1980
gtgaatgcct aatgttggct attgccgaag aattttttgg atttgttaag tgatcaacat   2040
gaaaagtgta gttttaagtt gattggtata aaatcggctg gtagtagcca aggcactta    2100 gtcagtcagt tgtgttccaa agcgttcaga acacattgcc atatttcttt acttatttct   2160
tcttgctcgt ggttaaaaaa cacaaaactc agacaaaatg tgtgacgatg aggttgctgc   2220
tttggtcgtt gataatggtc cggt                                           2244
```

<210> SEQ ID NO 2
<211> LENGTH: 21
<212> TYPE: DNA
<213> ORGANISM: Artificial Sequence
<220> FEATURE:
<223> OTHER INFORMATION: BmAldegF Primer

<400> SEQUENCE: 2
gatgtgygac gaygatgttm g    21

<210> SEQ ID NO 3
<211> LENGTH: 22
<212> TYPE: DNA
<213> ORGANISM: Artificial Sequence
<220> FEATURE:
<223> OTHER INFORMATION: BmAldegF Primer

```
<220> FEATURE:
<221> NAME/KEY: misc_feature
<222> LOCATION: 13
<223> OTHER INFORMATION: n = a, c, g or t

<400> SEQUENCE: 3
cttctcsagg gangtggagg cg                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic
<220> FEATURE:
<223> OTHER INFORMATION: Mexmuf1R

<400> SEQUENCE: 4
cattrtcaac raccaragca gca                                             23

<210> SEQ ID NO 5
<211> LENGTH: 2582
<212> TYPE: DNA
<213> ORGANISM: Bombyx mori

<400> SEQUENCE: 5
gccataggac atgacactgt ggaagtaact aaagtaaact aaacgagccg tgtccgcatt      60
tgttaacatt ctaatttttt ttactgcgta tgctgcagag ctaagcttac tcgccaattt     120
atgaatatga ggtccccact gcagtttgga gtccactgtt ataccaagaa atacggttga     180
ctcaacaagc tccaatgatt cctcagaaac aattacatta ctatctactt gtctcacatt     240
taaagatgat ttaatacatt ttaaagtaaa tttaatacat ttcgttatta tttaattta      300 acgttatttt taatttaata cattgcggca tcacaattta ttgcttacgt ttccattgat     360
aaataaaccg taatgtatga gtagtattgt cgattgcatc gttcaatgcg cagatcgcct     420
gctagcggta ttggcatgca atcggatcaa tgaatcaatt gcaggtcaca gggcggttaa     480
atttaactcg acttgtcacc ggctaactgc atccgtggtg aagttcaatg tttgttttga     540
tactaaatcc gtttgttatg ttcattactt aaactccata tctatatatt aataggtgaa     600
ggaaaaactt tgtaccccctt tttacgaaaa ttgcgcggac ggatgagtat gaaatttctc     660
acacttaaag agaatataga gaaggagtgc acaatgctaa tatattttt aaatattcga      720 taaaagatac tttaaatcaa taaagaaaca attacacgca ctaccatgta gttgacacac      780
acacatataa tactctttgt ttattgcact gaagtattgt caaacttttg ttattgctta     840
aagtctgtag tcaaattgag ataggttag tattgtttat ctttaatatt acgagtattt      900
ttctatagtg tagtcttggc gaaatctgta acaataggac cataataatg ttgaaactta     960
taattcaatt aattatagtc gaatttcgac tactgcagga ccactagtat aaataattat    1020
atgaaaataa attaacatga tccattatta cgagaaaaac acacacacta catgatgcta    1080
agtaaagctt agaaatgccg tcacccattt tgagagctaa cgtggttgac atctccgcgg    1140
ctctacagcc cacctgacgc gggctctcct gtcgcgactc tacgatggcg tggagacggt    1200
aaccgcttac ggtggtgagt tagttaagtt tgccaacgac gacaatcaac attttcagat    1260
aaagaaacat atgtacttgc agtaaagtaa agttatacat tcgatgcgat ttgaacacat    1320
gtaaacatgt aacaaaaagt aggatgtttt tgactggcc cgcagctccc gtgggactaa     1380
gctgttactt tgagacatga ggtcaatgtc tgaattgtat gatacagttt acaggctccc    1440
```

-continued

```
tcactcctca aatacggatg catgttatgt atacgagacc tttaaaaatt tccgtaacta    1500
ctgtagatag agtgttctga acacacgctg acaggcagga atcctaccta cttcagcccc    1560
ccagggttca tgggttctgg cttaacatta gatgtgccac ctgcacaccg ttctatttaa    1620
actgaaaaat aaaattttag gcgaacgaca ccatccagtg aaatgatttg caataagcac    1680
ttcttatatg ccacgttact gtacatcata tattttttacc ccacatcagg gttaactcta    1740
cataggtaca taatatcact acatagtata aaacagagtc gctttctctg tccctatatc    1800
cctatgtatg cttaaatctt taaaactacg caacggattt ttatgcggtt gtttataata    1860
gatagagtga ttgaagagca aggtttatat gtataataac atccattaaa tagtggagaa    1920
atcaataata aattacagtt tccgaagcga agcgagggcg gatcgctagt aatattatta    1980 tttttttgc tggaaactat gcgtgttttt tcaaataata tatttcttt ttgggttgtt    2040 accaactcca attacatatc aggcgtcatt aaaaaatact acggaatttt gtggtctgaa    2100
taatatgtag gtattgatat taagcattgg tcatgttgtc tgatttaat gcttttatt    2160 tatttataat gtattgaatt cttagttatt atcagtttga agaattacaa aagtcaaata    2220
cctaaataaa atctatattt tttattcgca ttgtacatat ttctgaactc taagtacggt    2280
cgagcgcggc gcccatcgcc cgcaatggct cgcggcgcgc tcaaatcttt tcgcgattta    2340
atctgttttt aaccaattt cggtgcaaaa tattattgaa caataatcca aatctgttat    2400
ttatttatac agtaagttcg ttagacaggt aagttagtgt aattgtgtac atttcgcgtg    2460
tattatcgaa cgcgatcgtg gagaggcggg ggcgacccgg ctcgccttgt atggagcgcg    2520
gccgcggctc acgcgcgtcc tatataagaa accggcgccg ggaaccgccg cactcgcagt    2580
cc                                                                   2582
```

<210> SEQ ID NO 6
<211> LENGTH: 1768
<212> TYPE: DNA
<213> ORGANISM: Aedes aegypti

<400> SEQUENCE: 6

```
gttcgagcag tagacccacc aaccatagaa gtgattaaag aggctgttag tcagctgaag     60
aactgcagct gggaaggacg agatccctgt caaacttctc aaacacgaaa gtcctccgag    120
tatttctgaa ggtataggag ggcgaagaaa tgcccaccgg ctggtttgaa gaaaaaacac    180
agactggagt gcaacaatta caaaggata acagtgctca attcagcgta caaaatactg    240
tcgggcatct tgtcgaatag attgctcgag gagttaatcg tcgacgaata ccacgctggt    300
ttttgtgagg gctgctcgac aacggaccag atgtttacct tacgaatgac cttagataac    360
atccaggagt ttagcttgca gagtcaccat ctgtttattg atttcaaggc ggcgcacgat    420
tcaatgagaa gaaatgagct gtggcagata atgtctgaac atggttttcc gacgaaattg    480
atcaggctga tacgtgcaac atgctccttg gctttgcgga cgatatggac cttattggaa    540
tcggtcgaag atcagcgaag gaggccttcg tgcatcttga gagggagacg gattggcctt    600
actattaatt ctacccaaac aacaaatatg gtagatagag gtaggcctag tggtgctggt    660
actgaggtaa tctttgatgg ggatgtgttt gaagttatcg aagatttagt ttatttcgaa    720
gcacttgtga catgtgacaa tgacgtttct cgcgaaataa aaagacgtgt tggggctgcg    780
aatagggcgt tttacggact acgtaaccaa cttaagtcct gcaacttgca aacggaaaca    840
aaattcatcc tgtatgaaac aatgattcgc ccgatggctc tcctcgggca caaagcacgg    900
acattgaaag aagcagaccg acacttacag gtcaaataca tctatgcaac agaacttgat    960
```

```
tctcaactta tgagcacttt catagttata aaaattgaga gctttcttca tcaactaaca    1020
attttcgcat gtgtatgttg ctctggaaag tcgagtaaat ttccaattcg aaaaaattct    1080
cgaccggtgg gattcgaacc cacgagcctt tccttggtct tgctgaatag ctgtgaacgg    1140
tgaacgcacc gctacagcta tttgcacttt tctcgttttt ttttttttcaa aatcccaatg   1200 aaaatccttc aaaatgttgc acttcaattt ttgtacgttc tttgctcatg atgtaaattt    1260
catttgattt aatcactaat ttattgcttc caacatgagc aattttcga taaaaatgta     1320 ttccggaaac atgttcgcaa tacttgtcgc acaactaaga aaagtaacag gtgaaacatt    1380
ctctaatgat gctttcttgc gcgtgtgacg tcgcgacgac gacggcggcg gttcttctaa    1440 ccgttttgg caaaccgtca cgtcctgaaa agcggctacc cagtcacgca gcgcggcgga     1500
ggcaaaggta aaacactaca gctcggtcag ggatgagtaa ggacgagata aattaaaaat    1560
atgagaaatt cgtctcccag tcatgtttat tttagctcga aagtgagcga ttccttcccc    1620
gcgtggctgc gtcgtgtttt gttgtgatca attccaagtt tgggatcacg ggaagagcga    1680
gagagaaaga gttcgcgaga atttcagcac caaattggta ttagatagtg tcatgtgcac    1740
cgtatataaa ctttgagccc aaccgcca                                       1768
```

<210> SEQ ID NO 7  
<211> LENGTH: 23  
<212> TYPE: DNA  
<213> ORGANISM: Artificial Sequence  
<220> FEATURE:  
<223> OTHER INFORMATION: Synthetic  
<220> FEATURE:  
<223> OTHER INFORMATION: MexmuF1Rn

<400> SEQUENCE: 7

```
cagcaacatc rtcgtcgcac atc                                              23
```

<210> SEQ ID NO 8  
<211> LENGTH: 22  
<212> TYPE: DNA  
<213> ORGANISM: Artificial Sequence  
<220> FEATURE:  
<223> OTHER INFORMATION: Primer

<400> SEQUENCE: 8

```
gtgtagcgtg aagacgacag aa                                               22
```

<210> SEQ ID NO 9  
<211> LENGTH: 21  
<212> TYPE: DNA  
<213> ORGANISM: Artificial Sequence  
<220> FEATURE:  
<223> OTHER INFORMATION: Synthetic  
<220> FEATURE:  
<223> OTHER INFORMATION: MID

<400> SEQUENCE: 9

```
gacgacagaa agggcgtggt g                                                21
```

<210> SEQ ID NO 10  
<211> LENGTH: 20  
<212> TYPE: DNA  
<213> ORGANISM: Artificial Sequence  
<220> FEATURE:  
<223> OTHER INFORMATION: Synthetic  
<220> FEATURE:  
<223> OTHER INFORMATION: MexmuAcRn2

<400> SEQUENCE: 10
tcacaccgcg ctcatcgtca                                       20

<210> SEQ ID NO 11
<211> LENGTH: 23
<212> TYPE: DNA
<213> ORGANISM: Artificial Sequence
<220> FEATURE:
<223> OTHER INFORMATION: Synthetic
<220> FEATURE:
<223> OTHER INFORMATION: MexmuAcRn3

<400> SEQUENCE: 11
cacgttaatg ttgagctgca tgg                                   23

<210> SEQ ID NO 12
<211> LENGTH: 22
<212> TYPE: DNA
<213> ORGANISM: Artificial Sequence
<220> FEATURE:
<223> OTHER INFORMATION: Synthetic
<220> FEATURE:
<223> OTHER INFORMATION: MexmuAcRn4

<400> SEQUENCE: 12
atccgagcga gtcagcaaca ac                                    22

<210> SEQ ID NO 13
<211> LENGTH: 32
<212> TYPE: DNA
<213> ORGANISM: Artificial Sequence
<220> FEATURE:
<223> OTHER INFORMATION: Synthetic
<220> FEATURE:
<223> OTHER INFORMATION: AemuAcproAscF

<400> SEQUENCE: 13
ggcgcgccgt tcgagcagta gacccaccaa cc                         32

<210> SEQ ID NO 14
<211> LENGTH: 28
<212> TYPE: DNA
<213> ORGANISM: Artificial Sequence
<220> FEATURE:
<223> OTHER INFORMATION: Synthetic
<220> FEATURE:
<223> OTHER INFORMATION: AemuAcintSphR

<400> SEQUENCE: 14
gcatgctatg ccttaggaag ccctgccg                              28

<210> SEQ ID NO 15
<211> LENGTH: 31
<212> TYPE: DNA
<213> ORGANISM: Artificial Sequence
<220> FEATURE:
<223> OTHER INFORMATION: Synthetic
<220> FEATURE:
<223> OTHER INFORMATION: AemuAcintSphF

<400> SEQUENCE: 15
gcatgccgta tatcgagtgg caagctcgaa g                          31

<210> SEQ ID NO 16
<211> LENGTH: 34
<212> TYPE: DNA
<213> ORGANISM: Artificial Sequence

```
<220> FEATURE:
<223> OTHER INFORMATION: Synthetic
<220> FEATURE:
<223> OTHER INFORMATION: AemuAcproNheR

<400> SEQUENCE: 16
gctagccaac cgtctattcg catagtacaa ttcc                               34

<210> SEQ ID NO 17
<211> LENGTH: 793
<212> TYPE: DNA
<213> ORGANISM: Artificial Sequence
<220> FEATURE:
<223> OTHER INFORMATION: 5 prime UTR (including truncated intron in
      lower case) of number 4133

<400> SEQUENCE: 17
cggcattcat tctagttccg aaaccgtttg ccgtgccacg tgttcgcgat cgttctcatt     60
cgatcggagt gactgccgtt tgaggattag tgtgtgcaga agaaaccaac ggatagaagt    120
tcctttttgt gtgagtgtca ttggcctttg atggataatt aatgtggaaa tgattggata    180
tggtgtacta actgcattga ataaaatatt acataatgtg agaaagactc gaacaatgta    240
aattacgaaa atgaaaattg caaagatgaa acagttgaac gcttgaatga agagtacgtg    300
gagtgattca acaatgcaat atttaacatt gaacaaatct acaaaagtga ataatacgtt    360
aaaaaaaata agaatgcaat ggacgatttg gttgaagttt gacaaacaac atcaaatcgg    420
cagggcttcc taaggcatag catgccgtat atcgagtggc aagctcgaag ataccatatg    480
ctctggaaag tcgataaaat ttcctactag aaaagatcct cggctcgtgg gattcgaatc    540
cacgaccctc agcttcataa agaattctta ttttatacac aatgaagtaa aatttgtgtg    600
catacttcaa aattgtcttt gaagtgtagt tagtcattcc aacgttatca tattgtaata    660
ttatttatac taatctttaa agcacaaata ccatggtcca tatcggaaat tggcatacat    720
atggcatatg atataatgcc actaggttcc taacaaggga attgtactat gcgaatagac    780
ggttggctag cat                                                      793

<210> SEQ ID NO 18
<211> LENGTH: 702
<212> TYPE: DNA
<213> ORGANISM: Artificial Sequence
<220> FEATURE:
<223> OTHER INFORMATION: DNA sequence for ZsGreen of number 4133

<400> SEQUENCE: 18
atggcccagt ccaagcacgg cctgaccaag gagatgacca tgaagtaccg catggagggc     60
tgcgtggacg gccacaagtt cgtgatcacc ggcgagggca tcggctaccc cttcaagggc    120
aagcaggcca tcaacctgtg cgtggtggag ggcggcccct tgcccttcgc cgaggacatc    180
ttgtccgccg ccttcatgta cggcaaccgc gtgttcaccg agtaccccca ggacatcgtc    240
gactacttca agaactcctg ccccgccggc tacacctggg accgctcctt cctgttcgag    300
gacggcgccg tgtgcatctg caacgccgac atcaccgtga gcgtggagga gaactgcatg    360
taccacgagt ccaagttcta cggcgtgaac ttccccgccg acggcccggt gatgaagaag    420
atgaccgaca actgggagcc ctcctgcgag aagatcatcc ccgtgcccaa gcagggcatc    480
ttgaagggcg acgtgagcat gtacctgctg ctgaaggacg gtggccgctt gcgctgccag    540
ttcgacaccg tgtacaaggc caagtccgtg ccccgcaaga tgcccgactg cacttcatc     600 cagcacaagc tgacccgcga ggaccgcagc gacgccaaga accagaagtg gcacctgacc    660
```

```
gagcacgcca tcgcctccgg ctccgccttg ccctccggac tc                        702
```

<210> SEQ ID NO 19
<211> LENGTH: 675
<212> TYPE: DNA
<213> ORGANISM: Artificial Sequence
<220> FEATURE:
<223> OTHER INFORMATION: DNA sequence for DsRed2 of number 4014

<400> SEQUENCE: 19

```
atggcctcct ccgagaacgt catcaccgag ttcatgcgct tcaaggtgcg catggagggc       60
accgtgaacg gccacgagtt cgagatcgag ggcgagggcg agggccgccc ctacgagggc      120
cacaacaccg tgaagctgaa ggtgaccaag gcggccccc tgcccttcgc ctgggacatc       180
ctgtccccc agttccagta cggctccaag gtgtacgtga agcaccccgc cgacatcccc       240
gactacaaga agctgtcctt ccccgagggc ttcaagtggg agcgcgtgat gaacttcgag      300
gacggcggcg tggcgaccgt gacccaggac tcctccctgc aggacggctg cttcatctac      360
aaggtgaagt tcatcggcgt gaacttcccc tccgacggcc ccgtgatgca aaagaagacc      420
atgggctggg aggcctccac cgagcgcctg taccccgcg acggcgtgct gaagggcgag       480
acccacaagg ccctgaagct gaaggacggc ggccactacc tggtggagtt caagtccatc      540
tacatggcca agaagcccgt gcagctgccc ggctactact acgtggacgc caagctggac      600
atcacctccc acaacgagga ctacaccatc gtggagcagt acgagcgcac cgagggccgc      660
caccacctgt cctg                                                        675
```

<210> SEQ ID NO 20
<211> LENGTH: 228
<212> TYPE: DNA
<213> ORGANISM: Simian virus 40

<400> SEQUENCE: 20

```
taagatacat tgatgagttt ggacaaacca caactagaat gcagtgaaaa aaatgcttta       60
tttgtgaaat ttgtgatgct attgctttat ttgtaaccat tataagctgc aataaacaag      120
ttaacaacaa caattgcatt catttttatgt ttcaggttca gggggaggtg tgggaggttt     180
tttaaagcaa gtaaaacctc tacaaatgtg gtatggctga ttatgatc                   228
```

<210> SEQ ID NO 21
<211> LENGTH: 655
<212> TYPE: DNA
<213> ORGANISM: Anastrepha ludens

<400> SEQUENCE: 21

```
gtcttttgat tgtgaaagat ggtgaaatgc gttgatgcaa acatatgcca acaacaacag       60
cagcagcaac atcaacaata caacaactc tgcaaatagc cagcacaact gctcagactt       120
cgtgcaacga acaccaataa ccagcataac aaataccact acgcattcga gaactgcaat      180
tacaacaaca aaagaggcat taatagcaac aacaaaaatg agagtgcatg ctaattccaa      240
caaaagcaaa aactacagat atcaacaagg taatgagaat tcaacaaatg caataaatgg      300
cgcttccagt agcgaaagag aaggacacaa aaacaaaacc aatatataa agaaagcaat       360
ctctgaggaa atgcccatga gcgccatcta gcaattgaat cgctttacgt tgcatttgca      420
tgtgaacatt ttaattata tttcttttc tggattttat acaataaaat gcgtgtaaaa        480
ctgaaattta taaatttaac taacagaata tcaaggaaa attatgaaaa tgtagaaaaa       540
```

```
aattattaaa aattactaaa atccaaacaa atgaacatca aataattcac taataagagc    600
taattaagta aacatctttc cattgactaa ccaaggcaaa aatactaaaa gtaaa         655
```